United States Patent [19]

Sheth et al.

[11] Patent Number: 5,300,304
[45] Date of Patent: Apr. 5, 1994

[54] PULSATILE ONCE-A-DAY DELIVERY SYSTEMS FOR MINOCYCLINE

[75] Inventors: Nitin V. Sheth, Middletown; Joseph J. Valorose, Jr., Montgomery; Keith A. Ellway, Washingtonville; Madurai G. Ganesan, Suffern; Kieran G. Mooney, Warwick, all of N.Y.; Jerry B. Johnson, Upper River Saddle, N.J.

[73] Assignee: American Cyanamid Company, Wayne, N.J.

[21] Appl. No.: 892,383

[22] Filed: May 27, 1992

Related U.S. Application Data

[63] Continuation of Ser. No. 410,708, Sep. 21, 1989, abandoned.

[51] Int. Cl.⁵ .......................... A61K 9/14; A61K 9/16; A61K 9/54; A61K 9/58
[52] U.S. Cl. .................................... 424/490; 424/489; 424/494; 424/495; 424/497; 424/498; 424/458; 424/459; 424/461; 424/462
[58] Field of Search ............... 424/490, 452, 457, 458, 424/461, 462, 489, 494

[56] References Cited

U.S. PATENT DOCUMENTS

| | | | |
|---|---|---|---|
| 3,080,294 | 3/1963 | Shepard | 167/82 |
| 3,148,212 | 9/1964 | Boothe | 260/559 |
| 3,161,654 | 12/1964 | Shen | 260/319 |
| 3,226,436 | 12/1965 | Petisi | 260/559 |
| 3,356,571 | 12/1967 | Takesue et al. | 424/78.31 |
| 3,499,959 | 3/1970 | Corn | 424/496 |
| 3,865,935 | 2/1975 | Amann | 424/181 |
| 4,138,475 | 2/1979 | McAinsh | 424/19 |
| 4,173,626 | 11/1979 | Dempski | 424/19 |
| 4,250,166 | 2/1981 | Maekawa et al. | 424/81 |
| 4,353,887 | 10/1982 | Hess | 424/15 |
| 4,606,909 | 8/1986 | Bechgaard | 424/21 |
| 4,784,858 | 11/1988 | Ventouras | 424/468 |
| 4,837,030 | 6/1989 | Valorose | 424/456 |
| 5,133,974 | 7/1992 | Paradissis et al. | 424/494 |

FOREIGN PATENT DOCUMENTS

| | | |
|---|---|---|
| 2041222 | 10/1980 | United Kingdom . |
| 0327295 | 9/1989 | United Kingdom . |
| 0310814 | 12/1989 | United Kingdom . |

OTHER PUBLICATIONS

Physicians Desk Reference 1987 (43rd Ed)—Pages on Lederle Minocin—pp. 1487-1489.
Remington's Pharmaceutical Science, 1985, 17th Ed. pp. 278-1320.

Primary Examiner—Thurman K. Page
Assistant Examiner—James M. Spear
Attorney, Agent, or Firm—James V. Costigan

[57] ABSTRACT

Pharmaceutical delivery systems containing 7-dimethyl-6-deoxy-6-demethyltetracycline or a non-toxic acid addition salt thereof comprising mixtures or separate administration units of pH sensitive polymer coated spherical granules adapted to release the minocycline in a medium having a pH of in the range of from about 4.0 to about 7.5 and coated or uncoated quick release granules adapted to release minocycline in a medium having a pH of less than about 3.9 or minocycline powder, pH adapted multi-coated compositions and oral dosage unit form liquids, capsules or tablets containing the above are provided. These systems and formulations provide at least minimum therapeutic blood levels of minocycline for at least about 24 hours when administered to a subject only once-a-day. Methods for the preparation of the systems and formulations are provided as well.

34 Claims, 14 Drawing Sheets

PULSATILE ONCE-A-DAY DELIVERY SYSTEMS FOR MINOCYCLINE

This application is a continuation of Ser. No. 07/410,708 filed Sep. 21, 1989 now abandoned.

FIELD OF THE INVENTION

The invention relates to pharmaceutical delivery systems for the prolonged controlled release of 7-dimethylamino-6-deoxy-6-demethyltetracycline (minocycline) or non-toxic acid addition salts thereof. It provides a once-a-day delivery system which maintains therapeutic blood level concentrations of the medicament in a patient for twenty-four hours by the once-a-day administration of custom designed formulations comprising an initial loading or first pulse of minocycline powder or minocycline containing coated or uncoated quick release granules and a secondary loading or second pulse of minocycline containing pH sensitive polymer coated spherical granules either administered simultaneously or separately up to about 120 minutes apart. Multi-coated spheronized pharmaceutical compositions comprising initial and secondary minocycline loadings as well as oral dosage unit forms of all of the above are provided as well.

These pharmaceutical delivery systems, compositions and oral dosage unit forms will provide therapeutic plasma level concentrations of minocycline in the therapeutic range for effective antibacterial activity for up to about twenty-four hours.

BACKGROUND OF THE INVENTION

The tetracycline compound, 7-dimethylamino-6-deoxy-6-demethyltetracycline, and its non-toxic acid addition salts are widely used in therapy primarily for their antimicrobial effects. Commonly assigned Boothe et al, U.S. Pat. No. 3,148,212, and Pesti et al, U.S. Pat. No. 3,226,436, describe the preparation of minocycline. Although the compounds have achieved widespread use in oral dosage forms, they have several drawbacks.

The minimum therapeutically effective blood serum or plasma concentration level of minocycline in a human subject varies according to the organism causing the infection. The concentration is determined in vivo by clinical evaluation and in vitro by microbiological assays. Currently, the minimum therapeutically effective concentration is believed to be in the range of from about 0.1 to about 1.0 mcg of minocycline/ml of serum.

Organisms currently known to be susceptible to minocycline therapy include a wide range of gram-negative and gram-positive bacteria including, but not limited to agents of rickettsiae (Rocky Mountain spotted fever, typhus fever and the typhus group, Q fever, rickettsialpox, tick fevers); Mycoplasma pneumoniae (PPLO, Eaton agent); agents of psittacosis and ornithosis; agents of lymphogranuloma venereum and granuloma inguinale; the spirochetal agent of relapsing fever (Borrelia recurrentis); the agent of Lyme disease (Borrelia burgdorfeni), the agents of acne (Propionibacterium Corynebacterium acnes); the microorganisms Haemophilus ducreyi(chancroid), Yersinia pestis and Francisella tularensis, formerly Pasteurella pestis and Pasteurella tularensis, Bartonella bacilliformis, Bacteroides species, Vibrio comma and Vibrio fetus, Brucella species, Escherichia coli, Enterbacter aerogenes (formerly Aerobacter aerogenes), Shigella species, Mima species, Herellea species, Haemophilus influenzae (respiratory infections), Klebsiella species (respiratory and urinary infections), many Streptococcus species including strains of Streptococcus pyogenes and Streptococcus faecalis, Streptococcus pneumoniae, Staphylococcus aureus (skin and soft tissue infections), Neisseria gonorrhoeae, Neisseria meningitidis, Treponema pallidum and Treponema pertenue (syphilis and yaws), Listeria monocytogenes, Clostridium species, Bacillus anthracis, Fusobacterium fusiforme (Vincent's infection), Actinomyces species; and in the treatment of acute intestinal amebiasis and inclusion conjunctivitis. *Physician's Desk Reference*, 1987, Medical Economics Company, Oradell, N.J. (PDR 43rd Ed.).

Recent discovery shows that minocycline is absorbed at different rates in different portions of the gastrointestinal tract. Intubation studies in human patients have demonstrated that bioavailability of minocycline in the gastrointestinal tract, based upon 100 percent absorption in the stomach, is 106 percent in the duodenum, 80 percent in the jejunum and 58 percent in the ileum, indicating that minocycline demonstrates reduced absorption in the lower gastrointestinal tract.

The human stomach empties in about one hour in a fasting subject and in about one to about four hours with food. The half life of minocycline when taken without food is approximately 10 hours. When taken with food, the half life is extended to approximately 14 to 16 hours.

It has not been possible to achieve a once-a-day therapeutic blood level of minocycline using only delayed release granules of minocycline with or without food ingestion. Traditional pharmaceutical forms and traditional delayed release forms containing minocycline require frequent ingestion of multiple doses per day resulting in wide variations in serum concentration throughout the course of treatment and in poor patient compliance. This indicates a need for a custom designed once-a-day delivery system for minocycline to provide optimal therapeutic effect and patient compliance.

Shepard, U.S. Pat. No. 3,080,294, discloses a sustained release pharmaceutical tablet comprising an inner core coated with multiple layers of an active medicament mixture, each layer releasing a portion of active medicament as it is successively dissolved. Such layers are not pH adapted, however.

Amann, U.S. Pat. No. 3,865,935, discloses erythromycin tablets which are stable outside the stomach but which produce immediate action upon disintegration in the stomach. These tablets require sodium citrate or sodium citrate dihydrate and do not yield a controlled release of prolonged duration.

McAinsh et al, U.S. Pat. No. 4,138,475, disclose that propranolol or a pharmaceutically acceptable salt thereof can be formulated into a sustained release pharmaceutical composition by mixing with a non-water-swellable microcrystalline cellulose and forming into spheroids. These spheres are coated with a heavy film of hydroxypropyl methylcellulose and/or a plasticizer to eliminate any release of the drug in the stomach. The film coated spheroids are then filled into gelatin capsules. Apart from the fact that propranolol is used as a beta-blocker to treat heart problems and not for oral antimicrobial use, there is no hint or suggestion in McAinsh et al that the pharmaceutical compositions should be used with tetracycline compounds.

Dempski, et al, U.S. Pat. No. 4,173,626, disclose capsules comprising uncoated indomethacin (U.S. Pat. No 3,161,654) pellets for immediate release, coated indomethacin pellets for prolonged release, and non-medicated pellets as volume fill. Indomethacin is a prostaglandin synthetase inhibitor and is not an antibacterial agent. Furthermore, the coatings are not pH adapted.

Hess, et al, U.S. Pat. No. 4,353,887, disclose a divisible tablet comprising medicament containing granules wherein the surface area of the tablet is not materially increased by division.

In Bechgaard, U.S. Pat. No. 4,606,909, the placement of a sparingly soluble active substance, such as tetracycline, in an oral controlled release dosage form is disclosed. The sparingly soluble active substance must be used with a dispersion-enhancing substance, such as an anionic detergent, to promote solubility in intestinal fluids. The composition is formed into small spheres and enteric coated to eliminate any release of drug in the stomach. The coated spheres are tabletted or loaded into capsules. There is no teaching that such a dosage form can be used to provide a once-a-day delivery system of therapeutically effective amounts of 7-dimethylamino-6-deoxy-6-demethyltetracycline or its nontoxic acid addition salts, and particularly a delivery system which is not dependent upon the ingestion of food. Moreover, the requirement of a dispersion-enhancing substance, especially an anionic detergent, is a negative factor.

In Ventouras, U.S. Pat. No. 4,784,858, a controlled release tablet comprising (1) coated cores, not necessarily spheronized, comprising a core of a water-soluble pharmaceutically active substance dispersed in a water-insoluble polymeric excipient and a swellable water-insoluble polymeric substance; and (2) a coating of an elastic, water insoluble and semi-permeable diffusion film of a polymer is disclosed. Here, the core is made to expand with water, causing the surface of the coating to extend, making it permeable, and thereby releasing the medicament in the core.

U.K. Patent Publication No. GB 2,041,222 discloses the tabletting of microcapsules of indoprofen. Other active medicaments may be included in the tablet. The microcapsules are not formed by spheronization, and these tablets are only suitable for high dosage delivery.

The incorporation of water insoluble medicament containing spheroids comprised of microcrystalline cellulose and at least one cellulose derivative into capsules, sachets, and cachets is disclosed in U.K. Patent Publication No. GB 2,202,143. Sustained released is accomplished by the necessary inclusion of the cellulose derivative.

Parke-Davis has recently offered for use by the medical profession, capsules under the trademark DORYX ® containing specially coated pellets of doxycycline hyclate for oral administration. See, PDR 43rd Ed. (Pages 1487-1489) In contrast to minocycline hydrochloride and its isomers and analogs, doxycycline hyclate does not contain an alkyl amino group at either the 7- or the 9-position. The Parke-Davis pellets are said to comprise lactose, microcrystalline cellulose and povidone (polyvinylpyrrolidone) in addition to the doxycycline compound. The disclosure in PDR 43rd Ed. is unclear as to the advantages for using such film coated pellets, but it is believed that the film is used to minimize release in the stomach and any resulting gastric distress and not to provide a once-a-day dosage form.

Valorose et al, U.S. Pat. No. 4,837,030, disclose hard gelatin or soft gelatin capsules filled with minocycline comprising spherical granules.

Abandoned U.S. patent application Ser. No. 07/410,707 filed Sep. 21, 1989, discloses tablets comprising active spherical granules containing medicaments including tetracycline compounds and compressible spherical granules.

Abandoned U.S. patent application Ser. No. 07/410,709 filed Sep. 21, 1989, discloses hard shell and soft shell capsules filled with carbonic anhydrase inhibitor containing spherical granules.

It has now been discovered that a specific minocycline composition can be formulated to provide at least minimum therapeutic serum levels of the minocycline in a human subject for about 24 hours through once-a-day two pulse administration systems, comprising an initial loading component providing the first pulse which is absorbed up to 100 percent in the stomach and a secondary loading component providing the second pulse which is absorbed up to 100 percent in the duodenum and the upper part of the small intestine.

These formulations can also be processed into liquid, capsule, or tablet oral dosage unit forms.

SUMMARY OF THE INVENTION

Figure 1:
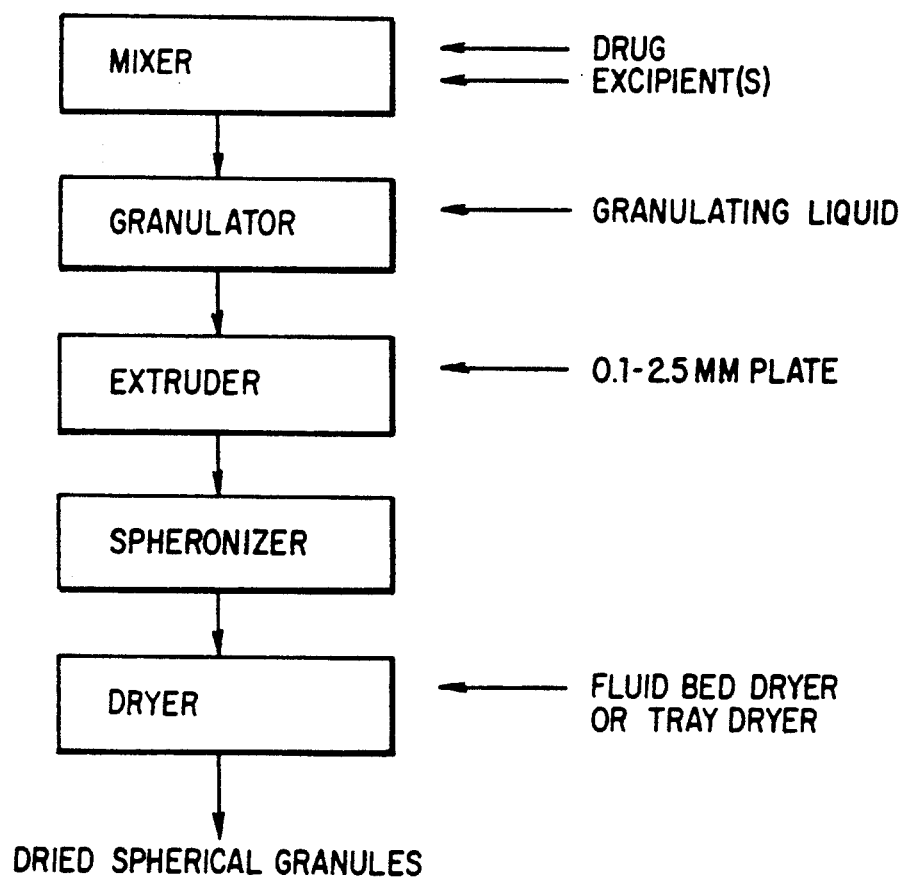
FIG. 1 is a graphic illustration of a method for the production of uncoated quick release granules and precursors of pH sensitive polymer coated spherical granules according to the present invention.

According to the present invention, there are provided pharmaceutical delivery systems adapted to provide a therapeutically effective blood concentration level of 7-dimethylamino-6-deoxy-6-demethyltetracycline or a non-toxic acid addition salt thereof for a sustained period of time of up to about twenty-four hours in a single dose comprising (I) a multiple delivery vehicle system comprising (A) an initial loading therapeutically effective number of quick release granules which comprise (a) (i) an effective amount of at least one pharmaceutically acceptable excipient; and (ii) an effective antibacterial amount of 7-dimethylamino-6-deoxy-6-demethyltetracycline or a non-toxic acid addition salt thereof, on or in the quick release granules; and optionally (b) a substantially uniform polymer coating, on the quick release granules and which is rapidly and substantially completely erodible in a medium having a pH of less than about 3.9; the quick release granules being adapted to release substantially completely the minocycline in a medium having a pH of less than about 3.9; (A-1) an initial loading therapeutically effective amount of a finely divided powder comprising (a) an effective antibacterial amount of 7-dimethylamino-6-deoxy-6-demethyltetracycline or a non-toxic addition salt thereof; and optionally (b) an independent effective amount of at least one pharmaceutically acceptable excipient which may be the same as or different than (I)(A)(a)(i); or (A-2) an initial loading therapeutically effective combination of (A) and (A-1); and (B) a secondary loading therapeutically effective number of pH sensitive polymer coated spherical granules which comprise (a) (i) an independent effective amount of at least one pharmaceutically acceptable excipient which may be the same as or different than (I)(A)(a)(i) or (I)(A-1)(b); and (ii) an independent effective antibacterial amount of 7-dimethylamino-6-deoxy-6-demethyltetracycline or a non-toxic acid addition salt thereof, on or in the coated spherical granules; and (b) a substantially uniform pH sensitive polymer coating, the polymer of which may be the same as or different than (I)(A)(b), on the coated spherical granules and which is substantially completely erodible in a medium having a pH in the range of from about 4.0 to about 7.5; the coated spherical granules thereby being adapted to release substantially completely the minocycline in a medium having a pH in the range of from about 4.0 to about 7.5; or (II) one or more multi-coated spheronized pharmaceutical single delivery vehicle compositions comprising (A) a core comprised of (a) a full or a partial secondary loading therapeutically effective antibacterial amount of 7-dimethylamino-6-deoxy-6-demethyltetracycline or a non-toxic acid addition salt thereof; or (b) at least one granule comprised of (i) an effective amount of at least one pharmaceutically acceptable excipient; and (ii) a full or a partial secondary loading therapeutically effective antibacterial amount of 7-dimethylamino-6-deoxy-6-demethyltetracycline or a non-toxic acid addition salt thereof, on or in said granule; having applied thereon (B) a substantially uniform pH sensitive polymer coating which is rapidly and substantially completely erodible in a medium having a pH in the range of from about 4.0 to about 7.5; the core thereby being adapted to release substantially completely the minocycline in a medium having a pH in the range of from about 4.0 to about 7.5; having applied thereon (C) a quick release coating comprising a full or a partial initial loading therapeutically effective antibacterial amount of 7-dimethylamino-6-deoxy-6-demethyltetracycline or a non-toxic acid addition salt thereof; and optionally having applied thereon (D)(a) a substantially uniform polymer coating, the polymer of which may be the same as or different than (B), and which is rapidly and substantially completely erodible in a medium having a pH of less than about 3.9; (b) a polymer overcoat, the polymer of which may be the same as or different than (B) or (D)(a); or (c) a combination of (a) and thereon (b).

The invention further contemplates oral dosage units in the form of pharmaceutically acceptable liquid carriers containing the above compositions or systems, hard or soft shell capsules at least partially filled with the above compositions or systems, and tablets formed from the above compositions or systems.

The invention also provides methods of maintaining a therapeutic level of the minocycline in the blood stream of a warm-blooded mammal for about 24 hours comprising the ingestion of the pharmaceutical delivery systems or oral dosage units above. The initial loading component can be administered up to about 120 and preferably up to about 60 minutes before the secondary loading component or the two components can be administered simultaneously.

A preferred embodiment of the present invention contemplates a pharmaceutical delivery system comprising a mixture of (A) an initial loading therapeutically effective number of quick release granules which comprise (a) (i) an effective amount of at least one pharmaceutically acceptable excipient; and (ii) an effective antibacterial amount of 7-dimethylamino-6-deoxy-6-demethyltetracycline or a non-toxic acid addition salt thereof, on or in the quick release granules; and optionally (b) a substantially uniform polymer coating which is rapidly and substantially completely erodible in a medium having a pH of less than 3.9; the quick release granules being adapted to release substantially completely the minocycline in a medium having a pH of less than about 3.9; and (B) a secondary loading therapeutically effective number of pH sensitive polymer coated spherical granules which comprise (a) (i) an independent effective amount of at least one pharmaceutically acceptable excipient which may be the same as or different than (A)(a)(i); and (ii) an independent effective antibacterial amount of 7-dimethylamino-6-deoxy-6-demethyltetracycline or a non-toxic acid addition salt thereof, on or in the coated spherical granules; and (b) a substantially uniform pH sensitive polymer coating, the polymer of which may be the same or different than (A)(b), on the coated spherical granules and which is rapidly and substantially completely erodible in a medium having a pH in the range of from about 4.0 to about 7.5; the coated spherical granules thereby being adapted to release substantially completely the minocycline in a medium having a pH in the range of from about 4.0 to about 7.5.

Additionally, the invention provides methods of maintaining therapeutic levels of 7-dimethylamino-6-deoxy-6-demethyltetracycline or a non-toxic acid addition salt thereof in the blood stream of a warm-blooded mammal for about 24 hours comprising the ingestion of an initial loading therapeutically effective number of the quick release granules either simultaneously with, or followed sequentially within up to about 120 minutes and preferably up to about 60 minutes, by the ingestion of a secondary loading therapeutically effective number of the pH sensitive polymer coated spherical granules in the delivery systems or oral dosage unit forms.

A method for the preparation of a pharmaceutical delivery system is provided comprising the steps of:

(A) forming an initial loading component by (a) blending (i) an effective amount of at least one pharmaceutically acceptable excipient; and (ii) an effective antibacterial amount of 7-dimethylamino-6-deoxy-6-demethyltetracycline or a non-toxic acid addition salt thereof; (b) granulating; (c) extruding; (d) spheronizing the resultant extrudate to form quick release granules which are adapted to release substantially completely the minocycline in a medium having a pH of less than about 3.9; (e) drying; and optionally (f) coating the quick release granules with a substantially uniform polymer coating which is rapidly and substantially completely erodible in a medium of a pH of less than about 3.9; or (A-1) forming an initial loading component by (a) dividing 7-dimethylamino-6-deoxy-6-demethyltetracycline or a non-toxic acid addition salt thereof into a fine powder; and optionally (b) mixing the powder with an effective amount of a pharmaceutically acceptable excipient; and (B) forming a secondary loading component by (a) blending (i) an independent effective amount of at least one pharmaceutically acceptable excipient which may be the same as or different than (A)(a)(i) or (A-1)(b); and (ii) an independent effective antibacterial amount of 7-dimethylamino-6-deoxy-6-demethyltetracycline or a non-toxic acid addition salt thereof; (b) granulating; (c) extruding; (d) spheronizing the resultant extrudate to form precursors of coated spherical granules; (e) drying; and (f) coating the precursors with a substantially uniform polymer coating, the polymer of which may be the same as or different than that in optional step (A)(f) and which is substantially completely erodible in a medium having a pH in the range of from about 4.0 to about 7.5.

Additionally, a method for the preparation of pharmaceutical compositions in oral dosage unit forms comprising a liquid comprising the additional step of mixing either the initial or the secondary loading component or both, either together or independently, with a pharmaceutically acceptable liquid carrier, comprising a capsule comprising the additional step of at least partially filling a hard or a soft shell capsule with either the initial or the secondary loading component or both, either together or independently, and optionally then sealing the capsules, and comprising a tablet comprising the additional optional step of adding a lubricant and the step of forming a tablet from either the initial or the secondary loading component or both, either together or independently, are provided.

A method is also provided for the preparation of multi-coated composition pharmaceutical delivery systems comprising the steps of forming a core from one or more spherical granules prepared by (a) blending (i) an effective amount of at least one pharmaceutically acceptable excipient; and (ii) a full or a partial secondary loading therapeutically effective antibacterial amount of 7-dimethylamino-6-deoxy-6-demethyltetracycline or a non-toxic acid addition salt thereof; (b) granulating; (c) extruding; (d) spheronizing the resultant extrudate to form one or more spherical granules; and (e) drying the spherical granules; (A-1) forming a core from a full or a partial secondary loading effective antibacterial amount of 7-dimethylamino-6-deoxy-6-demethyltetracycline or a non-toxic acid addition salt thereof; or (A-2) forming a core by coating a non-pareil seed or a sugar crystal with a full or a partial secondary loading therapeutically effective antibacterial amount of 7-dimethylamino-6-deoxy-6-demethyltetracycline or a non-toxic acid addition salt thereof; (B) coating the core with a substantially uniform polymer coating which is rapidly and substantially completely erodible in a medium having a pH in the range of from about 4.0 to about 7.5; the core thereby being adapted to release substantially completely the minocycline in a medium having a pH in the range of from about 4.0 to about 7.5; to form a single coated core; (C) coating the single coated core with a quick release coating comprising a full or a partial initial loading therapeutically effective antibacterial amount of 7-dimethylamino-6-deoxy-6-demethyltetracycline or a non-toxic acid addition salt thereof to form a multi-coated composition; and optionally (D) coating the multi-coated composition with (a) a substantially uniform polymer coating, the polymer of which may be the same as or different than (B) and which is rapidly and substantially completely erodible in a medium having a pH of less than about 3.9; (b) a polymer overcoat, the polymer of which may be the same as (B) or (D)(a); or (c), a combination of (a) and thereon (b).

The pharmaceutical delivery systems and the liquid, capsule and tablet oral dosage unit forms described above provide once-a-day prolonged effect controlled release forms of minocycline which maintain therapeutic blood levels for periods of up to twenty-four hours resulting in desirable and effective antibacterial therapy and less frequent administration to a subject. They also avoid high local concentrations in a system which may cause side effects such as gastroirritability.

DETAILED DESCRIPTION OF THE INVENTION

Novel pharmaceutical delivery systems have been discovered comprising mixed blends or separate administration units of an initial loading therapeutically effective number of coated and/or uncoated quick release granules and a secondary loading therapeutically effective number of pH sensitive polymer coated spherical granules, mixed blends or separate administration units of an initial loading therapeutically effective amount of finely divided minocycline powder and a secondary loading therapeutically effective number of pH sensitive polymer coated spherical granules, or multi-coated compositions. These systems and compositions can be formed into liquid, capsule, tablet or the like oral dosage unit forms as well. Many benefits can be realized from these novel delivery systems and oral dosage unit forms over conventional controlled release formulations. They result in a superiorly controlled and prolonged delivery of minocycline to a subject which in turn results in the ability of once-a-day dosages of 7-dimethylamino-6-deoxy-6-demethyltetracycline or non-toxic acid addition salts thereof in the compositions and oral dosage unit forms to sustain a desired blood level concentration in a subject for a relatively long period of time of up to twenty-four hours. Therefore, less frequent administration of the minocycline compound to a subject, possibly fewer and lessened side effects, including reduced gastroirritability, and better subject compliance with a medicament regimen are possible.

Oral dosage unit forms are those which are orally administered and contain medicaments which are absorbed into the blood stream from the alimentary tract.

An initial loading therapeutically effective amount of minocycline powder or number of quick release granules is that amount or number which provides an immediate or rapid and substantially complete release in a medium having a pH of less than about 3.9 and, preferably in a range of from about 1.0 to about 2.5, such as in the human stomach and thereby delivers and maintains a recommended dosage or concentration level of 7-dimethylamino-6-deoxy-6-demethyltetracycline or a non-toxic acid addition salt thereof to the blood stream or plasma of a subject within a recommended period of time and maintains that level, or a further recommended level for a further recommended period of time. This provides a first pulse of minocycline, preferably in the stomach, which quickly attains therapeutic plasma drug levels, i.e. at least that amount determined by in vivo clinical evaluation or in vitro microbiological assay to treat successfully infections caused by the invading organism or organisms.

A secondary loading therapeutically effective amount of minocycline powder or number of pH sensitive polymer coated spherical granules is that amount or number which provides a controlled release in a medium having a pH in the range of from about 4.0 to about 7.5 and preferably from about 4.0 to about 6, as in the human upper intestinal tract and particularly in the duodenum, and thereby delivers and maintains a further recommended dosage or concentration level of 7-dimethylamino-6-deoxy-6-demethyltetracycline or a non-toxic acid addition salt thereof to the blood stream or plasma of a subject within an independent recommended period of time and maintains that level or a different recommended level for an independent additional recommended period of time. This second pulse provides a delayed release and a controlled release of minocycline, preferably in the duodenum, which extends therapeutic plasma drug levels initially achieved by the first pulse, i.e. at least that amount determined effective for the particular organism causing the infection as described above, for a total prolonged period of time, i.e. up to about 24 hours.

The initial loading of the minocycline can be achieved by the administration of quick release granules containing the minocycline, by a finely divided powder of minocycline, by other compositions containing the minocycline compound, or by the quick release coating of one or more multi-coated compositions. The secondary loading can either be administered simultaneously, as in mixed blends of initial loading and secondary loading components or in one or more multi-coated compositions or in the oral dosage unit forms derived therefrom, or sequentially, after the initial loading generally within up to about 120 minutes and preferably within up to about 60 minutes, in separate administration units of initial and secondary loading components. The total period of time this therapeutic plasma drug level is maintained, i.e. from the combined effect of the two different types of granules, from the multi-coated compositions or from any other initial loading components administered simultaneously or prior to the pH sensitive polymer coated spherical granules of the pharmaceutical delivery systems or the oral dosage unit forms of the present invention, is preferably about 24 hours. Therefore, only one dosage unit will provide effective antimicrobial therapy for an entire day, the total therapeutic amount, i.e. the initial loading therapeutically effective amount or number plus the secondary loading therapeutically effective number, being that amount and/or number which will achieve and will maintain at least a therapeutically effective concentration of 7-dimethylamino-6-deoxy-6-demethyltetracycline or a non-toxic acid addition salt thereof/ml of serum or plasma in the blood serum or plasma of a human subject for about 24 hours.

The salts of minocycline useful in the present invention are the non-toxic acid addition salts, e.g. sulfonic, trichloroacetic, hydrochloric acid salts.

The last named compound is also known as minocycline hydrochloride. Typically, minocycline hydrochloride has been administered orally in a daily dosage of about 100 to about 400 mg in at least two and often more divided doses a day in a normal adult human being. It is commercially available in many forms under the tradename Minocin ® from Lederle Laboratories—Wayne, N.J. (PDR 43rd Ed.).

It should additionally be noted that minocycline hydrochloride readily undergoes epimerization and oxidative degradation to epiminocycline, a pharmacologically inactive and undesirable tetracycline compound. The amount of the epimer should be minimal but may range as high as from about 1.5 percent to about 10 percent without affecting the intended once daily dose of the present invention.

Preferably, the pharmaceutical delivery systems and oral dosage unit forms of the present invention will contain from about 25 mg to about 400 mg of 7-dimethylamino-6-deoxy-6-demethyltetracycline or non-toxic acid addition salt thereof and most preferably from about 80 mg to about 280 mg. Preferably, the ratio of initial loading component, i.e. minocycline powder, quick release granules, quick release coating or the like, to the secondary loading component, i.e. pH sensitive polymer coated spherical granules or single coated core, ranges from about 20:80 to about 80:20 by weight of initial loading component and secondary loading component combined and most preferably from about 30:70 to about 70:30. Preferably, the initial loading component, the secondary loading component, or both independently contain from about 20 to about 200 mg of minocycline.

The rapid and substantially complete release of the initial loading component is such that the initial loading component releases greater than about 70 percent and preferably greater than about 80 percent of the minocycline in less than about 90 minutes and preferably less than about 60 minutes in a medium of aqueous buffer, e.g. hydrochloric acid and/or acetate buffer, having a pH of less than about 3.9. Therefore, any polymer coating of the initial loading component must be specifically rapidly and substantially erodible or dissolvable to permit the initial loading component to meet these conditions.

The rapid and substantially complete release of the secondary loading component or single coated core is such that the secondary loading component or single coated core releases greater than about 50 percent and preferably greater than about 70 percent of the minocycline in less than about 90 minutes in a medium of aqueous buffer, e.g. acetate and/or phosphate buffer, having a pH in the range of from about 4.0 to about 7.5. Therefore, the pH sensitive polymer coating must be specifically rapidly and substantially completely erodible or dissolvable to permit the secondary loading component or single coated core to meet these conditions.

Further preferred embodiments of the present invention provide additionally that either from about 5 to about 20 percent of the minocycline in the secondary loading component or single coated core is released in about 2 hours when suspended in a medium of simulated gastric fluid having a pH of about 1.2 at about 37° C. or from about 20 to about 50 percent of the minocycline in the secondary loading component or single coated core is released in about 2 hours when suspended in a medium of simulated gastric fluid having a pH of about 1.2 at about 37° C.

The drug is released when it may be determined by a standard assay.

Many pharmaceutical excipients will be suitable for use in this invention. Judicious selection will be easy with the requirements and the test procedures mentioned herein kept in mind. An excipient with a known degree of solubility and swellability in the respective juices of the stomach and the upper small intestine, particularly the duodenum, should be used. Such excipients in either the quick release granules, the pH sensitive polymer coated spherical granules, the core or a combination of any of the foregoing include lactose, other mono- or di-saccharides, microcrystalline cellulose, starch, sodium carboxymethyl cellulose, hydroxypropyl cellulose, hydroxyethyl cellulose, crosscarmellose sodium, pregelatinized starch, polyvinylpyrrolidone, cross-linked polyvinylpyrrolidone, hydroxypropyl methylcellulose, cellulose acetate, hydroxypropyl methylcellulose phthalate, polyvinyl acetate phthalate, microcrystalline cellulose in combination with lactose, microcrystalline cellulose in combination with sodium carboxymethyl cellulose, microcrystalline cellulose in combination with crosscarmellose sodium, mixtures of any of the foregoing and the like as well as others with which those of ordinary skill in the art will be familiar, most of which are listed in standard references, for example, *Remington's Pharmaceutical Sciences*, 1985, 17th Edition, Philadelphia College of Pharmacy and Science, Chapter 68, Pharmaceutical Necessities, pages 1278–1320.

Although a single excipient can be used, e.g., microcrystalline cellulose, desirable results may require more care in selecting an appropriate amount of minocycline to be used in the spheres. Therefore, combinations of more than one excipient may be desirable.

Suitable forms of microcrystalline cellulose are, for example, the materials sold as Avicel ® PH-101 and Avicel ® PH-105 (available from FMC Corporation—American Viscoe Division, Avicel Sales, Marcus Hooks, Penna., U.S.A.). Avicel ® PH-101 is characterized as having an average particle size of 50 um, particle size specification of +60 mesh less than 1 percent and +200 meshless than or equal to 30.0 percent, moisture specification of less than 5.0 percent and acceptable flow properties. Avicel ® PH-105 is characterized as having an average particle size of 20 um, particle size specification of +400 mesh less than or equal to 1.0 percent, moisture specification of less than 5.0 percent, and poor flow properties.

A suitable mixture of microcrystalline cellulose and sodium carboxymethyl cellulose is, for example, the material sold as Avicel ® RC-581 by FMC Corporation. Avicel ® RC-581 is characterized as having an average particle size of less than 0.2 micron, particle size specification of 60 mesh less than or equal to 0.1 percent, and moisture specification of less than 6 percent.

The term "spheres" is well known in the pharmaceutical art, and means spherical granules having a diameter in the range of from about 0.1 to about 2.5 millimeters, preferably from about 0.5 to about 2 millimeters, and most preferably from about 0.8 to about 1.2 millimeters. Preferably, the quick release granules are spherical as well. If spheres having the medicament as a surface layer are to be prepared, coated seeds, e.g., non-pareil seeds or sugar crystals, may be used. Such non-pareil seeds are generally of about 0.1 mm to about 2.0 mm in size and typically are about 1.0 millimeter in size. They can comprise, for example, a blend of sugar and starch. Such crystals are generally 0.01 mm to about 0.1 mm in size. The cores of the multi-coated composition are preferably such seeds. However, the cores may comprise minocycline alone or in combination with the excipient as well.

The quick release granules typically are uncoated. However, they may be optionally coated with a polymer coating which is rapidly and substantially completely erodible in a medium having a pH of less than about 3.9 and particularly in the human stomach, thereby leaving their immediate or quick release characteristics relatively unchanged.

The film forming polymer, if used, can vary widely in type and amount which correlates into film or coating thickness. Illustrative but not limiting quick release spherical granule coating polymers are methyl cellulose, ethylcellulose, hydroxyethyl cellulose, hydroxypropyl cellulose, hydroxypropyl methylcellulose, hydroxypropyl methylcellulose phthalate, cellulose acetate phthalate, hydroxypropyl methylcellulose succinate, polymers and copolymers of (meth)acrylic acid or (meth)acrylic acid methyl ester, polyvinyl acetate phthalate or polymers or copolymers of polyvinyl acetate, cellulose acetate, fatty acids and esters thereof, cellulose acetate trimellitate, and mixtures of any of the foregoing, adapted to substantially completely dissolve in a medium having a pH of less than about 3.9. The coatings can include conventional additives, such as plasticizers, pigments, colorants, etc. The plasticizers include mineral oil, high boiling esters, vegetable oils and the like.

Commercial coating compositions found to be useful include Eudragit ®, a product of Rohm Pharma, Westerstadt, Germany, which comprises an anionic polymerizate of methyacrylic acid and methyl methacrylate; Surelease ® a product of Colorcon, Inc., West Point, Penna., which comprises an aqueous dispersion of ethylcellulose, dibutyl sebacate, oleic acid, fumed silica, and ammonium hydroxide; Aquacoat ®, a product of FMC Corp., which comprises an aqueous dispersion of ethylcellulose; Coateric ®, a product of Colorcon, Inc., which comprises polyvinyl acetate phthalate; Aquateric ®, a product of FMC Corp., which comprises cellulose acetate phthalate; Eastman ® C-A-P TM, a product of Eastman Kodak Company, Rochester, N.Y., which comprises cellulose acetate phthalate; and Eastman ® C-A-T, a product of Eastman Kodak Company, which comprises cellulose acetate trimellitate. Preferred as a coating material for the quick release granules is hydroxypropyl methylcellulose.

Although up to about 1 to about 10 parts by weight gain due to the coating based upon the weight of the uncoated quick release granules is suitable, from about 2 to about 5 parts by weight gain is preferred and about 2 parts by weight gain is most preferred.

This polymer coating may also optionally include a precoat, an overcoat or a combination of the foregoing. For best results, a 1 to 10 parts by weight gain level is preferred in addition to the standard coating when using aqueous coating formulations.

The polymer coating of the coated spherical granules is pH sensitive and is rapidly and substantially completely erodible in a medium having a pH in the range of from about 4.0 to about 7.5, particularly in the human upper small intestine and most particularly in the duodenum, thereby inhibiting erosion in a pH outside that range such as in the human stomach but leaving the rapid, controlled release characteristics of the coated spherical granules unaffected after the polymer coating is eroded in the upper small intestine, i.e. duodenum.

This pH sensitive film forming polymer can also vary widely in type and amount which correlate to film or coating thickness.

Illustrative but not limiting coated spherical granule pH sensitive coating polymers are methylcellulose, ethylcellulose, hydroxyethyl cellulose, hydroxypropyl cellulose, hydroxypropyl methylcellulose, hydroxypropyl methylcellulose phthalate, cellulose acetate phthalate, hydroxypropyl methylcellulose succinate, a polymer or copolymer of (meth)acrylic acid or (meth)acrylic acid methyl ester, polyvinyl acetate phthalate or polymers or copolymers of polyvinyl acetate, cellulose acetate, fatty acids and esters thereof, cellulose acetate trimellitate, and mixtures of any of the foregoing adapted to dissolve substantially completely in a medium having a pH of from about 4.0 to about 7.5 and preferably from about 4.0 to about 6. These coatings can include any of the conventional coating additives from above as well.

Commercial coating compositions found to be useful include Eudragit ® (Rohm Pharma, Westerstadt, Germany), Surelease ® (Colorcon, Inc., West Point, Penna.), Aquacoat ® (FMC Corp.), Coateric ® (Clorcon, Inc.), and Aquateric ® (FMC Corp.), Eastman ® C-A-P TM (Eastman Kodak Company), and Eastman TM C-A-T (Eastman Kodak Company). A suitable form of ethylcellulose is one having a viscosity in the range of 5 to 100 cps at 20° C. (U.S. National Formulary XIII) (content of ethoxy groups 44 to 51 percent by weight), and more particularly a viscosity of 50 cps at 20° C. (content of ethoxy groups 48 to 49 percent by weight). A suitable form of hydroxypropyl methylcellulose is one having a viscosity in the range of 3 to 100 cps at 20° C. (U.S. National Formulary XIII), and more particularly a viscosity of 6 cps at 20° C. Preferred as the coating is hydroxypropyl methylcellulose phthalate or a combination of hydroxypropyl methycellulose phthalate and hydroxypropyl methylcellulose, and most preferably, these coatings will be adapted to dissolve substantially completely in a medium having a pH of about 5.0 or greater than about 5.5.

Although from about 5 to about 35 parts by weight gain due to the pH sensitive polymer coating based upon the weight of the uncoated spherical granules (precursors of coated spherical granules) or core is suitable, from about 5 to about 25 parts by weight gain is preferred and from about 10 to about 25 parts by weight is most preferred.

The polymer coating may also independently include a precoat, an overcoat, or a combination of the foregoing. For best results, a 1 to 10 parts by weight gain level is preferred in addition to the standard coating when using an aqueous formulation.

The amounts of minocycline and excipient which comprise the quick release granules can vary broadly but will usually be in the range of from about 10 to about 70 parts by weight of minocycline and from about 90 to about 30 parts by weight of excipient based upon 100 parts by weight of minocycline and excipient combined. Preferably, the quick release granules comprise about 50 parts by weight of minocycline and about 50 parts by weight of excipient based upon 100 parts by weight of minocycline and excipient combined.

The amounts of minocycline and excipient which comprise the precursors of the pH sensitive polymer coated spherical granules or the core of the multicoated compositions can also vary broadly but will usually be in the range of from about 10 to about 80 parts by weight of minocycline and from about 90 to about 20 parts by weight of excipient based upon 100 parts by weight of minocycline and excipient combined. The amount of pH sensitive polymer coating on the precursors or the core varies broadly as well and is described above. Preferably, the coated spherical granules or core will comprise about 60 parts by weight of minocycline and about 40 parts by weight of excipient based upon 100 parts by weight of minocycline and excipient combined, and the pH sensitive polymer coating will comprise a weight gain of about 10 to about 25 parts by weight based upon 100 parts by weight of minocycline and excipient combined.

Additionally, the amount of quick release granules or initial loading component and the amount of pH sensitive polymer coated spherical granules, single coated core or secondary loading component in the pharmaceutical delivery systems, oral dosage unit forms or multi-coated compositions will vary broadly, but will generally be in the range of 20 to about 80 parts by weight of quick release granules or initial loading component and about 80 to about 20 parts by weight of pH sensitive polymer coated spherical granules, single coated core or secondary loading components, based upon 100 parts by weight of quick release granules or initial loading component and pH sensitive polymer coated spherical granules, single coated core or secondary loading component combined. Most preferably, the quick release granules or initial loading component comprise from about 30 to about 70 parts by weight and the pH sensitive polymer coated spherical granules, single coated core, or secondary loading component comprise from about 70 to about 30 parts by weight based upon 100 parts by weight of quick release granules or initial loading component and pH sensitive polymer coated spherical granules, single coated core or secondary loading component combined.

The pH sensitive polymer coating in the multi-coated compositions generally comprises from about 5 to about 35 parts by weight gain based upon the weight of the core, preferably comprises from about 5 to about 25 parts by weight gain and most preferably from about 10 to about 25 parts by weight gain.

The optional overcoat comprises from about 1 to about 10 parts by weight gain in addition to the standard polymer coating when using an aqueous coating formulation.

The multi-coated compositions or the initial loading and/or the secondary loading components of the pharmaceutical delivery systems, separately or in combination, independently can be mixed with a pharmaceutically acceptable liquid carrier known to one of ordinary skill in the pharmaceutical arts such as diluting agents, emulsifying agents and suspending agents alone or with additional active medicaments, colorants, pigments, flavorings, additional excipients or a combination of any of the foregoing to provide an oral dosage unit form. The multi-coated spheronized pharmaceutical compositions are preferably suspended in a high density liquid pharmaceutical carrier to form a fluid suspension delivery system.

The multi-coated compositions or the components of the pharmaceutical delivery systems, separately or in combination, can also independently be filled into either hard shell gelatin or soft shell gelatin capsules alone or with additional active medicaments, lubricants, disintegrants, plasticizers, colorants, pigments, flavoring, additional excipients or a combination of any of the foregoing by any conventional capsule forming and/or filling machine and optionally may be sealed by any means commonly known to one of ordinary skill in the pharmaceutical arts including but not limited to spot-welding, gelatin bands and matched locking rings.

The hard shell capsules used in the present invention are generally comprised of gelatin, water and optionally, FD&C colorants, opacifying agents such as titanium oxide, sulfur dioxide to prevent any decomposition or a combination of any of the foregoing. They generally comprise two sections, one slipping over the other, completely surrounding the filling.

The soft shell capsules used in the present invention are generally a soft, globular, gelatin shell somewhat thicker than the shell of the hard shell capsule. The gelatin is usually plasticized by the addition of glycerin, sorbitol, or a similar polyol. They may also contain a preservative to prevent the growth of fungi.

The multi-coated compositions or the components of the pharmaceutical delivery systems, separately or in combination, can also independently be formed alone, or with the addition of lubricants, disintegrants, plasticizers, colorants, pigments, flavorings, additional active medicaments, pharmaceutically acceptable excipients, or a combination of any of the foregoing, into tablet oral dosage unit forms by conventional means known to one of ordinary skill in the pharmaceutical arts, e.g. compressing or pressing. The tablet may then, optionally, be coated with an overcoat as explained above.

All of the pharmaceutical delivery systems, compositions or oral dosage unit forms of the present invention can be prepared using any conventional pharmaceutical production equipment.

FIG. 1 illustrates the typical steps in the preparation of uncoated spherical granules for use as either uncoated quick release granules or as precursors of pH sensitive polymer coated spherical granules. Firstly, an effective amount of at least one pharmaceutically acceptable excipient and an effective antibacterial amount of 7-dimethylamino-6-deoxy-6-demethyltetracycline or a non-toxic acid addition salt thereof are blended in a mixer. The resultant blend of the first step is granulated with a liquid medium, e.g. an aqueous solution or an organic solvent and preferably water, until the proper consistency for extrusion is realized. The resultant granulated mass is then extruded in an extruder or extruder/spheronizer, through a suitably sized, e.g. 1.0 mm, perforated plate and is spheronized at high speed for a time sufficient to form spherical granules. The wet spherical granules are then dried in conventional equipment at suitable temperatures, e.g. such as tray dryers at 55° to 65° C. or a conventional fluid bed dryer system at 65° to 70° C. to a low moisture level, e.g. about 1 to about 7 percent and preferably about 2 to about 5 percent.

Figure 2:
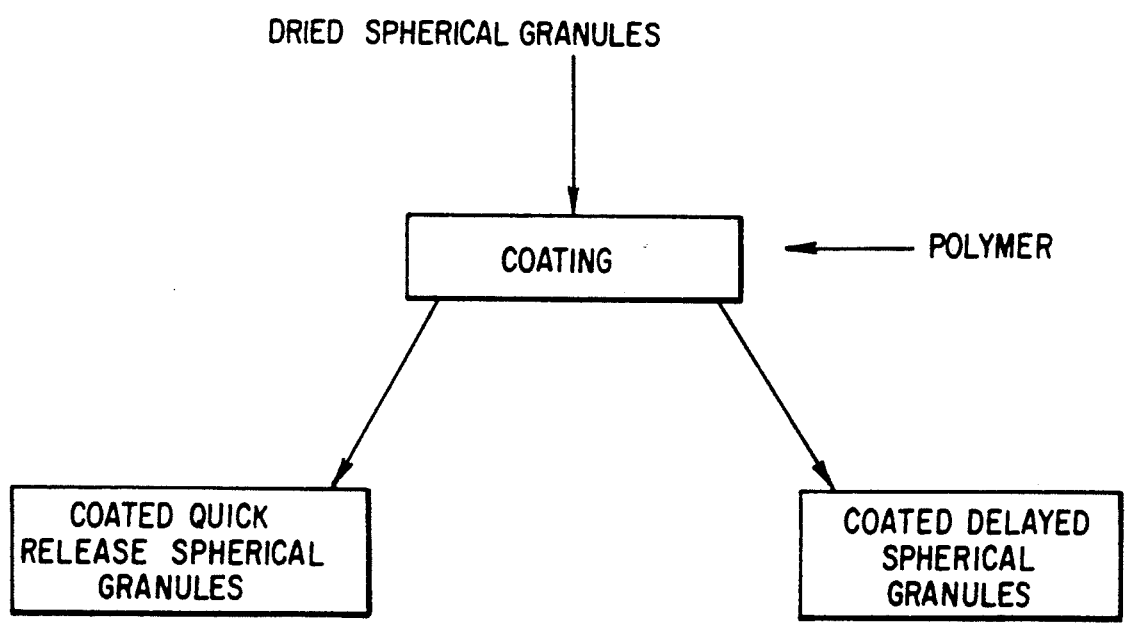
FIG. 2 is a graphic illustration of a method for the production of coated quick release granules and pH sensitive polymer coated spherical granules according to the present invention.

FIG. 2 illustrates that the quick release granules then, optionally, may be coated with a substantially uniform polymer coating which is rapidly and substantially completely erodible in a medium having a pH of less than about 3.9 with an aqueous or organic solvent, e.g. methylene chloride and/or methanol, solution of the desired coating forming polymer, using fluid bed technology, pan-coating or the like. Preferably, fluid beds are used. FIG. 2 also illustrates that the precursors of coated spherical granules are independently coated with a substantially uniform polymer coating which is rapidly and substantially completely erodible in a medium having a pH of from about 4.0 to about 7.5 in a manner as explained above.

An initial loading therapeutically effective number of uncoated quick release granules, coated quick release granules, an initial loading therapeutically effective amount of minocycline, or a combination thereof may then be mixed in a low shear mixer with a secondary loading therapeutically effective number of pH sensitive polymer coated spherical granules.

Figure 3:
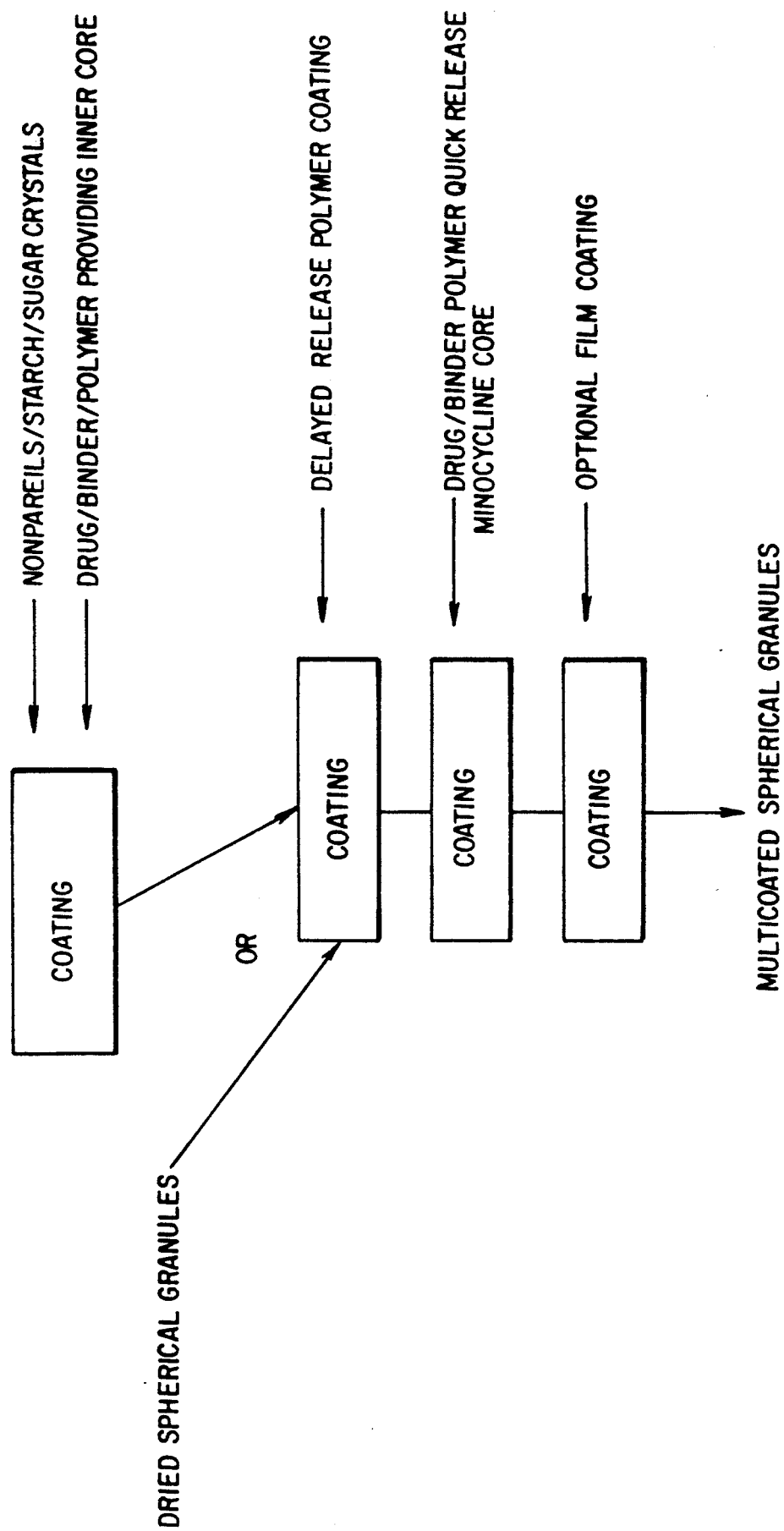
FIG. 3 is a graphic illustration of a method for the preparation of multi-coated once-a-day minocycline delivery system compositions according to the present invention.

FIG. 3 illustrates the typical steps in the preparation of the multi-coated compositions of the present invention. Firstly, a core is prepared comprising a dried spherical granule as illustrated in FIG. 1, minocycline coated non-pareil seeds, sugar crystals, or minocycline in combination with a suitable binder or pharmaceutically acceptable excipient. The core is then coated with a substantially uniform polymer coating which is rapidly and substantially completely erodible in a medium having a pH of from about 4.0 to about 7.5 in a manner as described above. An initial loading therapeutically effective amount of minocycline is then coated onto the single coated core in a manner as described above. Optionally, a polymer coating, an overcoating or a combination of the foregoing is sequentially applied in a manner as described above.

Figure 4:
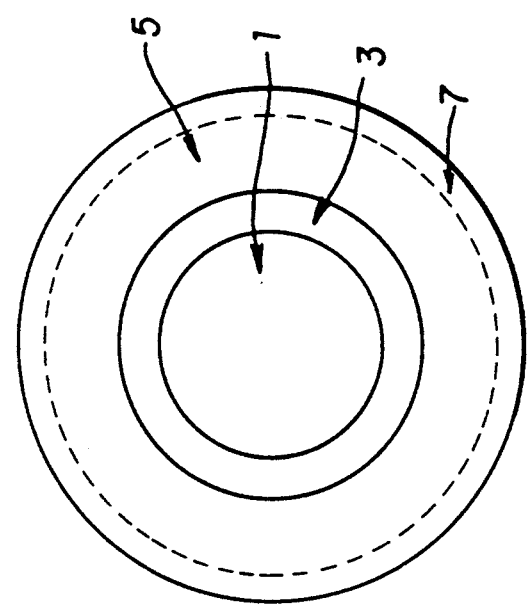
FIG. 4 is a graphic illustration of a multi-coated once-a-day minocycline delivery system having a minocycline core according to the present invention.

FIG. 4 illustrates the multi-coated composition prepared with a minocycline (1) core coated with a pH sensitive polymer coating (3) in turn coated with a quick release minocycline coating (5) and finally coated with an optional polymer coating which is rapidly and substantially completely erodible in a medium having a pH of less than about 3.9 (7).

Figure 5:
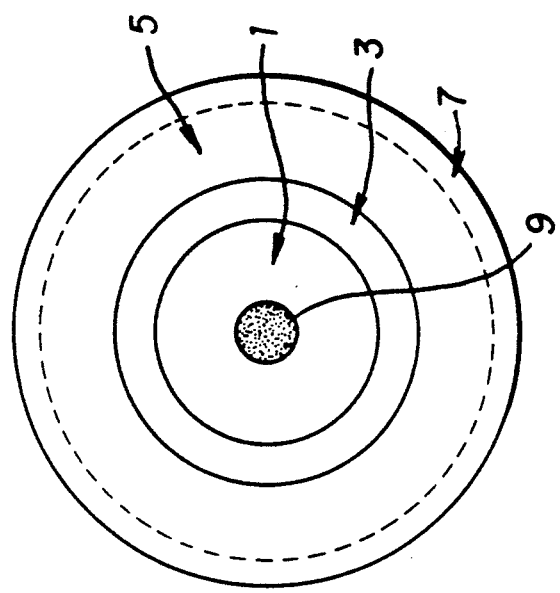
FIG. 5 is a graphic illustration of a multi-coated once-a-day minocycline delivery system having minocycline on a non-pareil seed core or sugar and/or starch crystal core according to the present invention.

FIG. 5 illustrates the multi-coated composition prepared from a non-pareil seed or sugar crystals (9) coated with minocycline (1) core, which is coated with a pH sensitive polymer coating (3), subsequently coated with a quick release minocycline coating (5), and finally coated with an optional polymer coating which is rapidly and substantially completely erodible in a medium having a pH of less than about 3.9 (7).

The mixture or separate units of initial and secondary loading components, or the multi-coated compositions may then optionally be mixed with a pharmaceutically acceptable liquid carrier.

Alternatively, a hard shell or a soft shell capsule may be at least partially filled and optionally sealed, as previously described, to form a capsule oral dosage unit form.

Tabletted oral dosage unit forms may be prepared by optionally adding a lubricant or other pharmaceutically acceptable excipient and then compressing or pressing.

The pharmaceutical delivery systems, spheronized pharmaceutical compositions, multi-coated compositions or oral dosage unit forms containing them may be administered by ingestion, thereby maintaining a therapeutic minocycline level in the blood stream of a warm blooded mammal for about 24 hours, and thereby providing about a 24 hour therapeutic blood level from a once-a-day dosaging system.

DESCRIPTION OF THE PREFERRED EMBODIMENTS

The following examples illustrate the invention without limitation. All parts are given by weight unless otherwise indicated. Bioavailability is a function of, and is an absolute term that indicates measurement of, both the true rate and the total amount (extent) of drug that reaches the blood stream from an administered dosage form.

EXAMPLE 1

A blend is prepared by mixing 2500 grams of minocycline hydrochloride powder (Minocin ®—Lederle Laboratories) and 2500 grams of microcrystalline cellulose (Avicel ® PH-101, FMC Corporation) in a Hobart mixer at low speed. The powder blend is then granulated to an extrudable consistency by adding 3000 ml of water slowly and mixing. The resultant granulate is extruded at high speed through a 1.0 mm plate in a NICA extruder/spheronizer Model S450, and subsequently is spheronized at high speed. The wet spheres are dried in an Aeromatic fluid bed dryer at 70° C. air input until the moisture content is about 1 to 7 percent to form uncoated quick release granules having a smooth surface and a homogeneous tetracycline compound distribution.

EXAMPLE 2

A polymer coating is prepared by mixing 71 parts of hydroxypropyl methylcellulose adapted to dissolve in a medium having a pH of less than about 3.9, 4 parts of sodium lauryl sulfate and 25 parts of mineral oil and then by adding 7 to 9 times the total weight of the above solids of water. The coating solution is substantially completely dissolvable in a medium having a pH of less than about 3.9. The solution is sprayed onto uncoated quick release granules prepared by the method of Example 1 to a 2 to 10 parts by weight gain based upon the weight of the uncoated quick release granules to form quick release granules having a coating which is adapted to erode rapidly and substantially completely in a medium having a pH of less than about 3.9.

EXAMPLE 3

A blend is prepared by mixing 3000 grams of minocycline hydrochloride powder (Minocin ®—Lederle Laboratories), 1650 grams of microcrystalline cellulose (Avicel ® PH-101, FMC Corporation) and 350 grams of AC-DI-SOL (crosscarmellose sodium) in a Hobart mixer at low speed. The powder blend is then granulated to an extrudable consistency by adding 3000 ml of water slowly and mixing. The resultant granulate is extruded at high speed through a 1.0 mm plate in a NICA extruder/ spheronizer Model S450, and subsequently is spheronized at high speed. The wet spheres are dried in an Aeromatic fluid bed dryer at 70° C. air input until the moisture content is about 1 to 7 percent to form precursors of coated spherical granules.

A pH sensitive polymer coating dissolvable in a medium having a pH of about 5.0 is prepared by mixing 75 parts of hydroxypropyl methylcellulose phthalate (HP-50, Shin-Etsu Chemical, Tokyo, Japan) adapted to dissolve in a medium having pH of about 5.0, 15 parts of mineral oil, and 10 parts of orange colorant (Opaspray K-1-2562, Colorcon, Inc., West Point, PA) and dissolving the mixture in an organic solvent.

The polymer coating solution is sprayed onto 900 grams of dried precursors of coated spherical granules at an initial rate of 7 ml/min which is gradually increased to 9 ml/min in an Uni-Glatt Model 82/E fluid bed until a 16 parts by weight gain based upon the weight of the precursors of coated spherical granules is achieved. Input air is adjusted to 54° C. while output air is adjusted between 22° and 25° C.

pH sensitive polymer coated spherical granules having a polymer coating adapted to erode rapidly and substantially completely in a medium having a pH of about 5.0 are formed.

Figure 6:
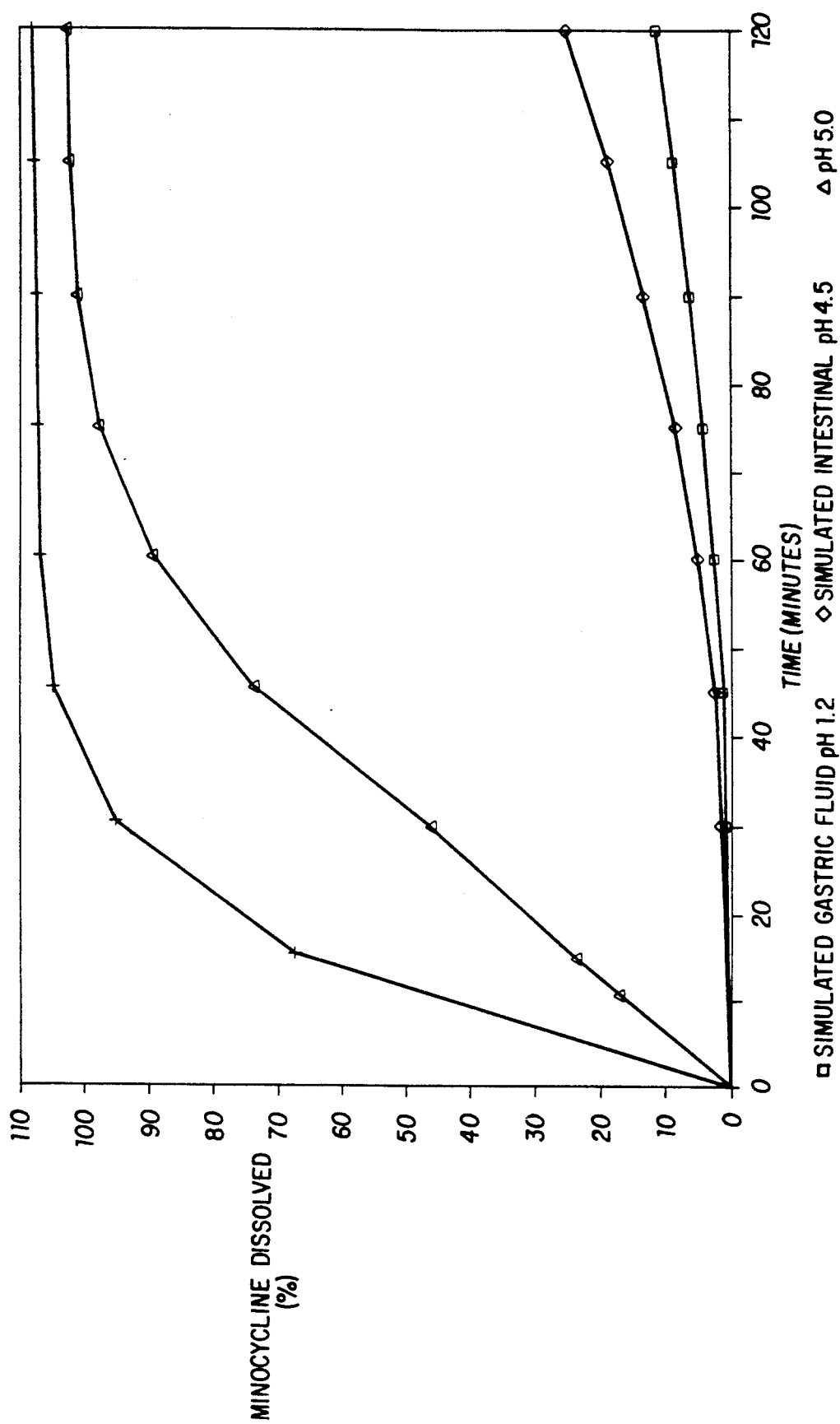
FIG. 6 is a graphic illustration of the release rate of minocycline from pH sensitive polymer coated spherical granules adapted to release the minocycline in a medium having a pH of about 5.0 according to the present invention.

Dissolution profiles of the minocycline hydrochloride are determined by U.S.P. XXI test methods using dissolution media of simulated gastric fluid having a pH of 1.2, of buffered media having pH's of 4.5 and 6.0, and of simulated intestinal fluid having a pH of 7.2. The results appear in FIG. 6 in graph form.

EXAMPLE 4

The procedure of Example 3 is followed, however, before the pH sensitive polymer coating is applied to the precursors of coated spherical granules, a precoating of hydroxypropyl methylcellulose is applied by spraying until about 1 to about 5 parts by weight gain based upon the weight of precursors of coated spherical granules is achieved. This provides a smooth surface on the precursors for subsequent pH sensitive polymer coating.

EXAMPLE 5

Coated spherical granules are prepared according to the procedure of Example 3. Subsequently, an overcoating of hydroxypropyl methylcellulose is applied by spraying until about 1 to about 5 parts by weight gain based upon the weight of the precursors of coated spherical granules is achieved.

EXAMPLE 6 pH sensitive polymer coated spherical granules with an undercoating are prepared according to the procedure of Example 4. Subsequently, an overcoating of hydroxypropyl methylcellulose is applied by spraying until about 1 to about 5 parts by weight gain based upon the weight of the non-overcoated but undercoated, precursors of coated spherical granules is achieved.

EXAMPLE 7

The procedure of Example 3 is followed substituting a pH sensitive polymer coating dissolvable at a pH of greater than about 5.5 which is prepared by mixing 75 parts of hydroxypropyl methylcellulose phthalate (HP-55, Shin-Etsu Chemical, Tokyo, Japan) adapted to dissolve in a medium having a pH of greater than about 5.5, 15 parts of mineral oil and 10 parts of orange colorant (Opaspray K-1-2562, Colorcon, Inc.) and dissolving the mixture in an organic solvent.

Figure 7:
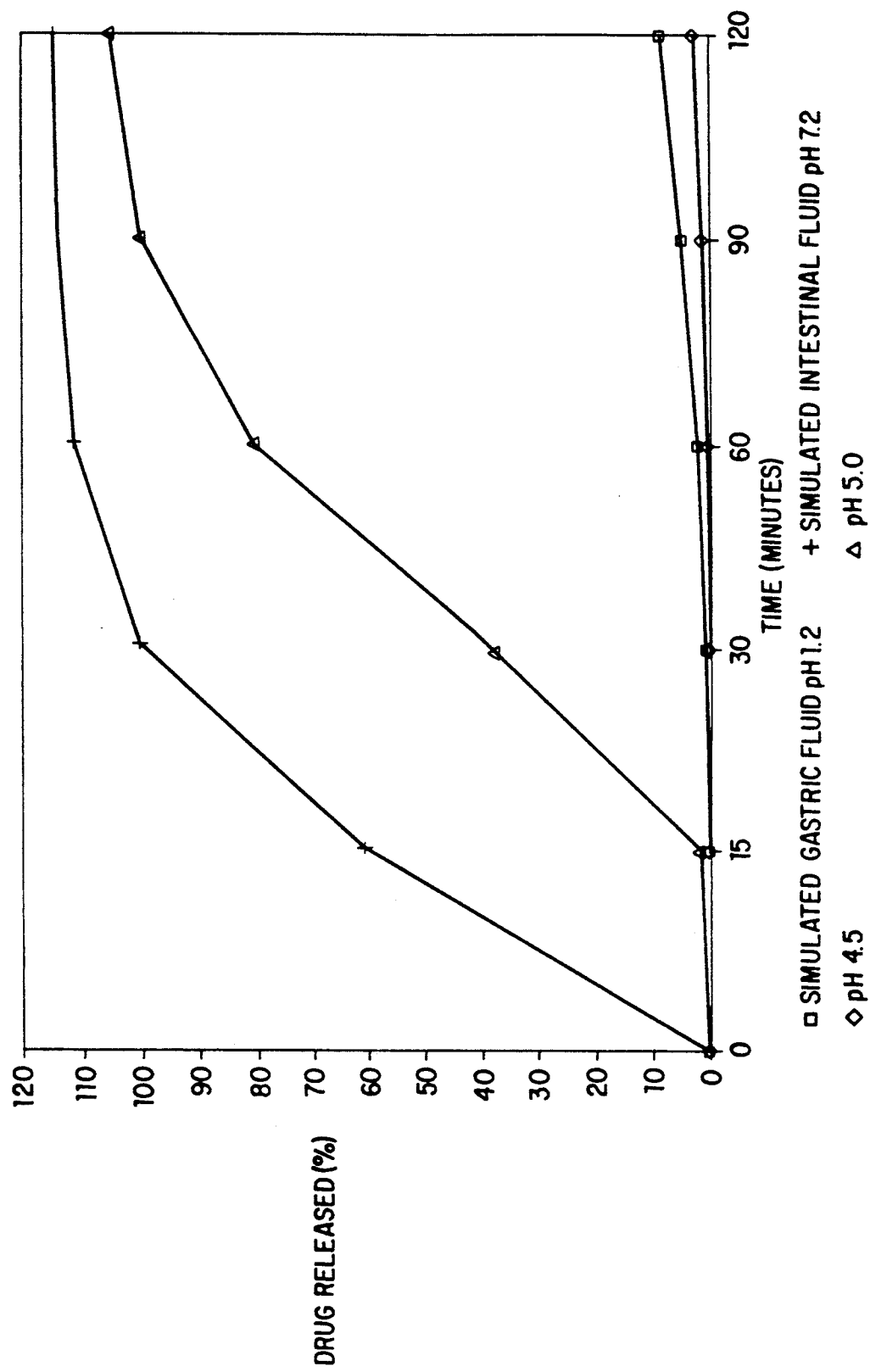
FIG. 7 is a graphic illustration of the release rate of minocycline hydrochloride from pH sensitive polymer coated spherical granules adapted to release the minocycline hydrochloride in a medium having a pH greater than about 5.5 according to the present invention.

Dissolution profiles of the minocycline hydrochloride are determined by U.S.P. XXI test methods using dissolution media of simulated gastric fluid having a pH of 1.2, of buffered media having pH's of 4.5 and 6.0, and of simulated intestinal fluid having a pH of 7.2. The results appear in FIG. 7 in graph form.

EXAMPLE 8

The procedure of Example 3 is followed substituting a pH sensitive polymer coating dissolvable in a medium having a pH of from about 4.0 to about 7.5 which is prepared by mixing 71.25 parts of hydroxypropyl methylcellulose phthalate (HPMCP-50, Shin-Etsu Chemical, Tokyo, Japan), 3.75 parts of hydroxypropyl methylcellulose (Shin-Etsu Chemical), 15 parts of mineral oil and 10 parts of orange colorant (Opaspray K-1-2562, Colorcon, Inc.) and dissolving the mixture in an organic solvent and spraying the polymer coating solution until a 10 parts by weight gain based upon the weight of the coated spherical granules is achieved.

Figure 8:
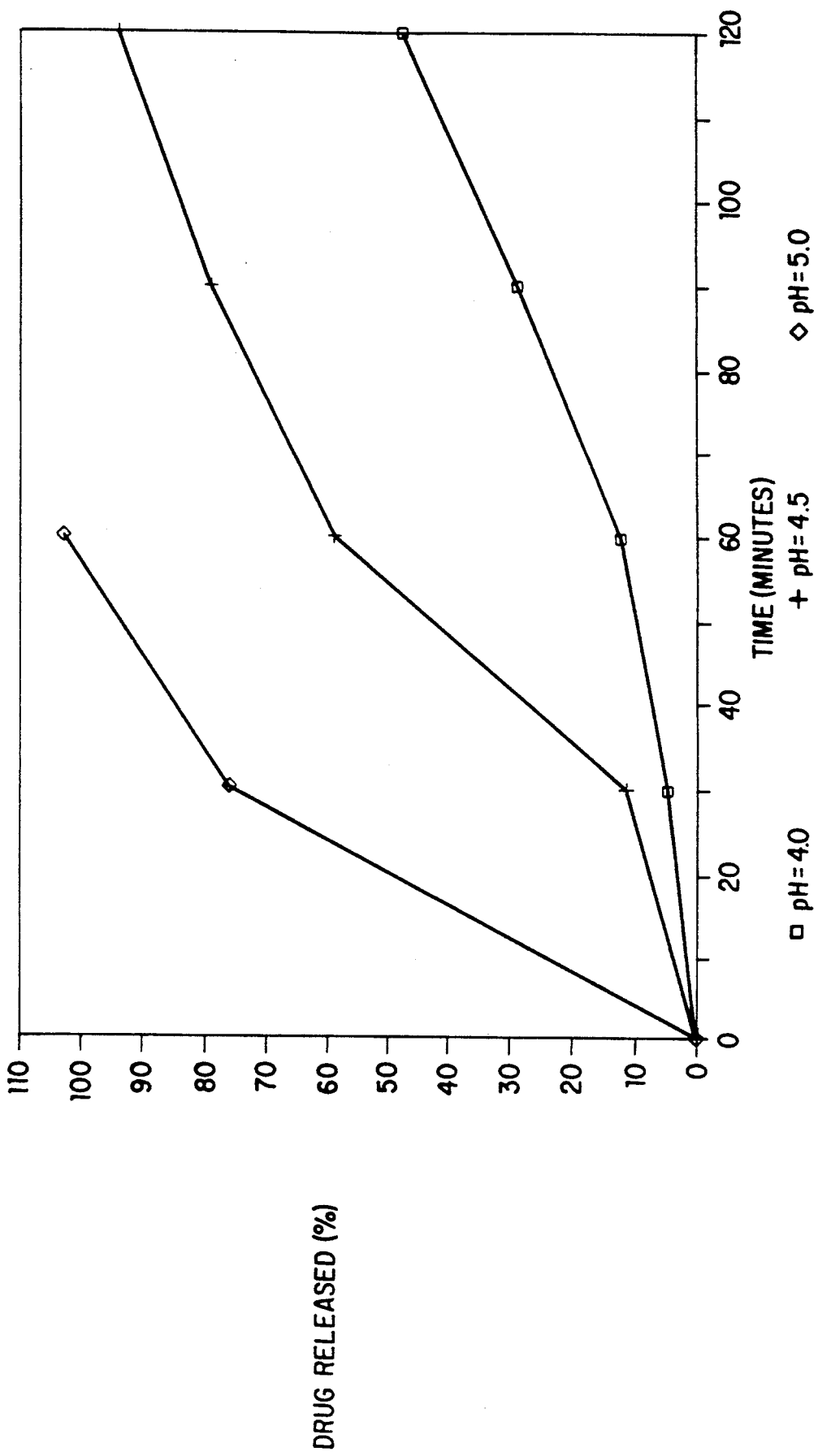
FIG. 8 is a graphic illustration of the release rate of minocycline from pH sensitive polymer coated spherical granules adapted to release the minocycline in a medium having a pH of about 4.0 to about 7.5 according to the present invention.

Dissolution profiles of the minocycline hydrochloride are determined by U.S.P. XXI test methods using buffered media having pH's of 4.0, 4.5 and 6.0. The results appear in FIG. 8 in graph form.

EXAMPLE 9

The procedure of Example 8 is followed, however the pH sensitive polymer coating is applied until a 20 parts by weight gain based upon the weight of the precursors of coated spherical granule is achieved.

EXAMPLE 10

The procedure of Example 3 is followed substituting a pH sensitive polymer coating dissolvable in a medium having a pH of from about 4.0 to about 7.5 which is prepared by mixing 60 parts of hydroxypropyl methylcellulose phthalate (HPMCP-50, Shin-Etsu Chemical, Tokyo, Japan), 15 parts of hydroxypropyl methylcellulose (Shin-Etsu Chemical), 15 parts of mineral oil and 10 parts of orange colorant (Opaspray K-1-2562, Colorcon, Inc.) and dissolving the mixture in an organic solvent and spraying the polymer coating solution until a 10 parts by weight gain based upon the weight of the precursors of coated spherical granules is achieved.

EXAMPLE 11

The procedure of Example 10 is followed, however the pH sensitive polymer coating is applied until a 20 parts by weight gain based upon the weight of the precursors of coated spherical granules is achieved.

Figure 9:
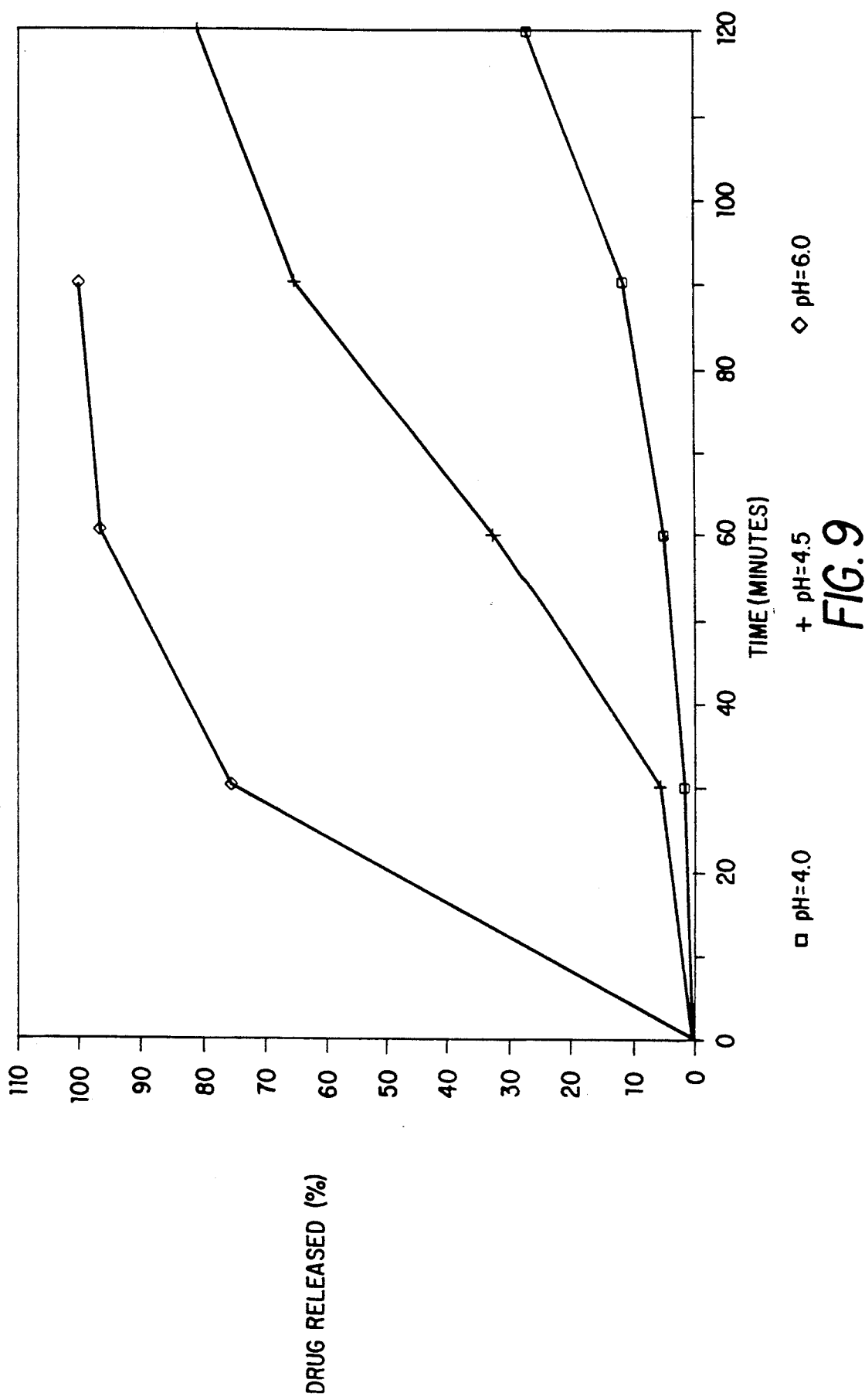
FIG. 9 is a graphic illustration of the release rate of minocycline from pH sensitive polymer coated spherical granules adapted to release the minocycline in a medium having a pH of about 4.0 to about 7.5 according to the present invention.

Dissolution profiles of the minocycline hydrochloride are determined by U.S.P. XXI test methods using buffered media having pH's of 4.0, 4.5 and 6.0. The results appear in FIG. 9 in graph form.

EXAMPLE 12 pH sensitive polymer coated spherical granules are prepared according to the method of Example 3. The resultant coated spherical granules are mixed with a pharmaceutically acceptable liquid medium to yield an oral dosage unit form.

EXAMPLE 13 pH sensitive polymer coated spherical granules are prepared according to the method of Example 3. The resultant coated spherical granules are filled into a hard shell capsule to yield an oral dosage unit form.

EXAMPLE 14 pH sensitive polymer coated spherical granules are prepared according to the method of Example 3. The resultant coated spherical granules are filled into a soft shell capsule to yield an oral dosage unit form.

EXAMPLE 15 pH sensitive polymer coated spherical granules are prepared according to the method of Example 3. The resultant coated spherical granules are compressed into a tablet to yield an oral dosage unit form.

EXAMPLE 16

The procedure of Example 3 is followed substituting an anionic polymerizate of methacrylic acid and methyl methacrylate (Eudragit ®—Rhom Pharma) for the pH sensitive polymer coating to form pH sensitive polymer coated spherical granules.

Figure 10:
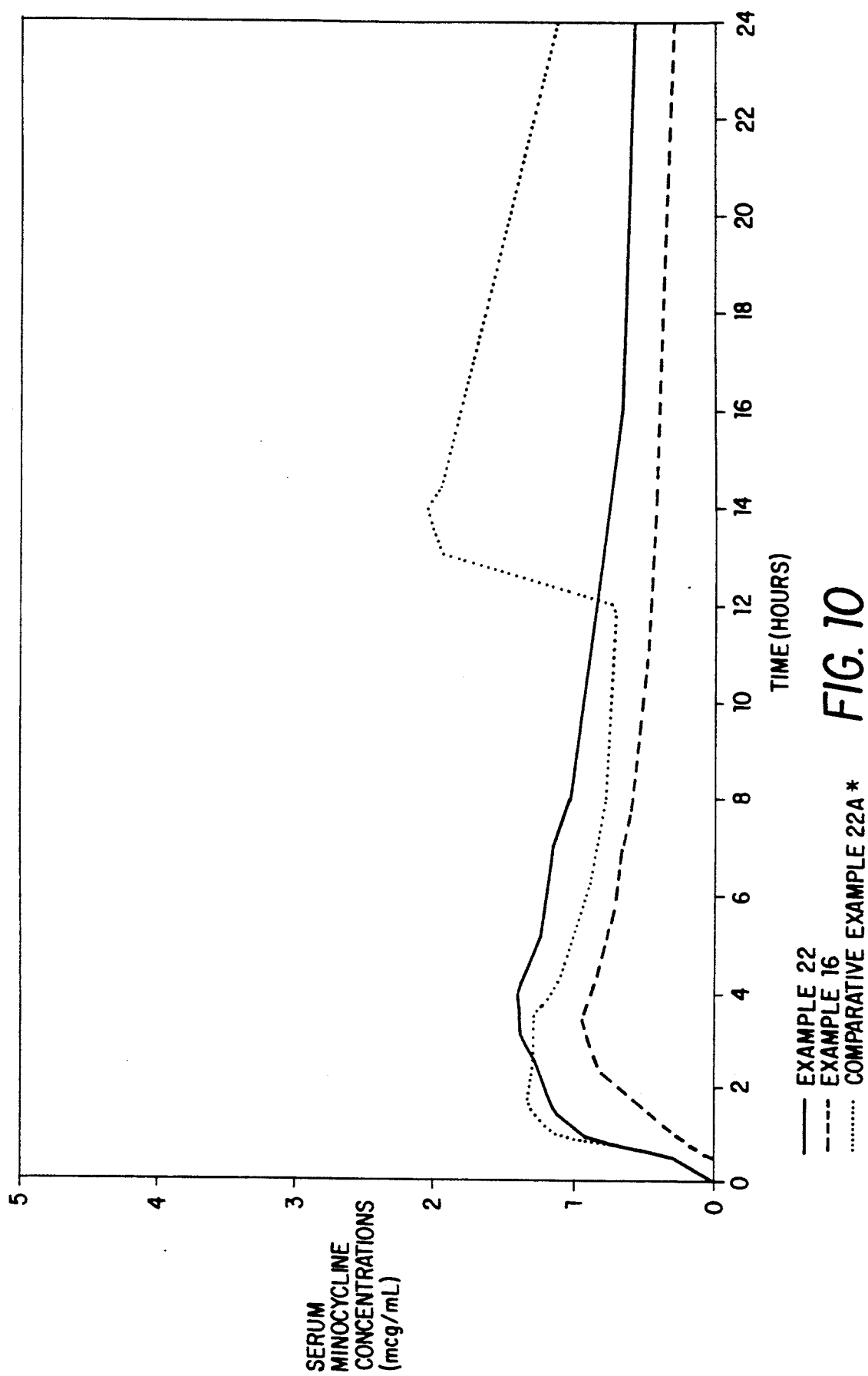
FIG. 10 is a graphic illustration of blood serum concentration levels of once-a-day administration of minocycline to human subjects in oral dosage unit forms according to the present invention and twice-a-day administration of minocycline in oral dosage unit form presently available from Lederle Laboratories.

A 185 mg sample of minocycline hydrochloride prepared according to the procedure of Example 16 is administered to a human subject, and serum concentration levels of minocycline hydrochloride are measured over a 24 hour period. The results appear in FIG. 10 in the curve referred to as "Example 16". These results show that in the absence of a quick release initial loading dose of minocycline, the blood level of minocycline drops below minimum therapeutically effective amounts desired for the majority of minocycline therapies after about 10-12 hours.

EXAMPLE 17

690 grams of quick release granules prepared by the method of Example 1 and 810 grams of the pH sensitive polymer coated spherical granules prepared by the method of Example 3 are mixed in a low shear blender at low speed for 15 minutes to form a spheronized pharmaceutical composition mixture.

EXAMPLE 18

The mixture prepared by the method of Example 7 is mixed with a pharmaceutically acceptable liquid carrier to form oral dosage unit forms having a total minocycline content of 185 mg, with 85 mg of minocycline contained in the quick release granules and 100 mg of the tetracycline compound contained in the pH sensitive polymer coated spherical granules.

EXAMPLE 19

The mixture prepared by the method of Example 7 is filled into hard shell gelatin capsules to form oral dosage unit forms having a total minocycline content of 185 mg, with 85 mg of minocycline contained in the quick release granules and 100 mg of the tetracycline compound contained in the pH sensitive polymer coated spherical granules.

Figure 11:
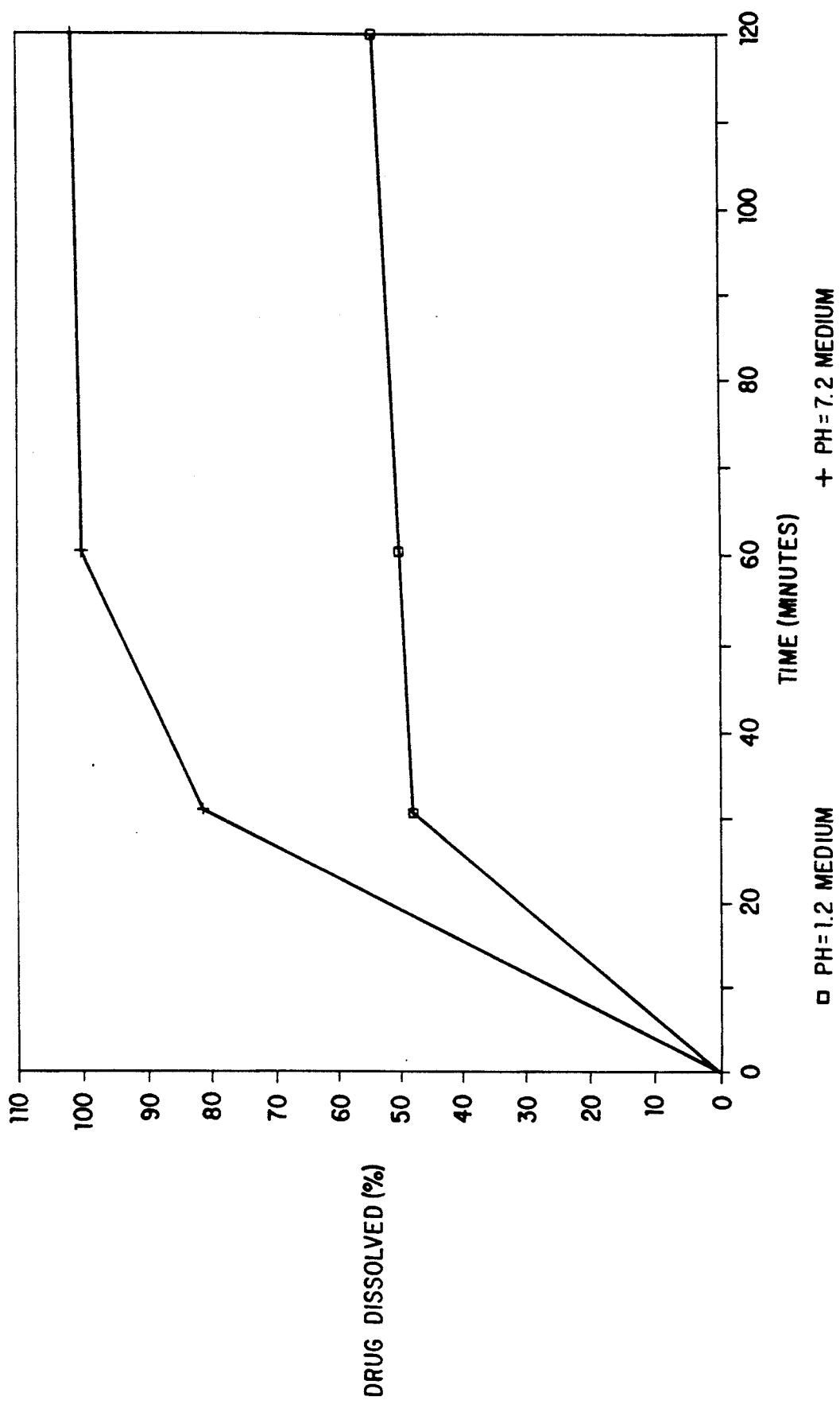
FIG. 11 is a graphic illustration of the release rate of minocycline from capsules containing a mixture of quick release granules adapted to release minocycline immediately in the stomach and pH sensitive polymer coated spherical granules adapted to release minocycline in a medium having a pH of about 5.0 in accordance with the present invention.

Dissolution profiles of the minocycline are determined by U.S.P. XXI test methods using dissolution media with pH's of 1.2 and of 7.2. The results appear in FIG. 11 in graph form.

Figure 13:
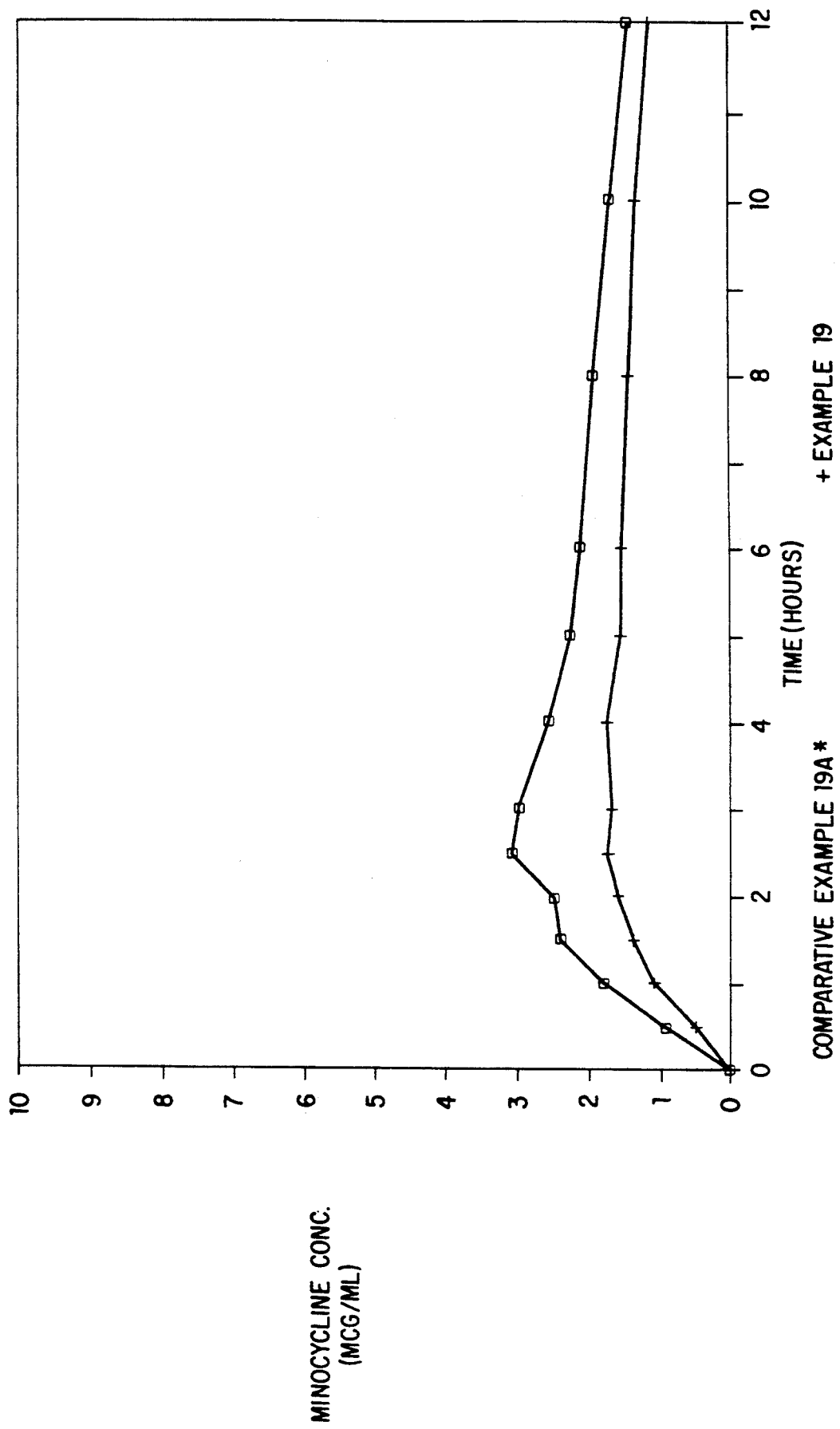
FIG. 13 is a graphic illustration of blood serum concentration levels on the first day of once-a-day minocycline administration to human subject in oral dosage unit form according to the present invention and single administration of two oral dosage unit form presently available from Lederle Laboratories.

Serum concentration levels of minocycline over the initial 12 hour period also appear in FIG. 13 in the curve referred to as "Example 19".

Figure 12:
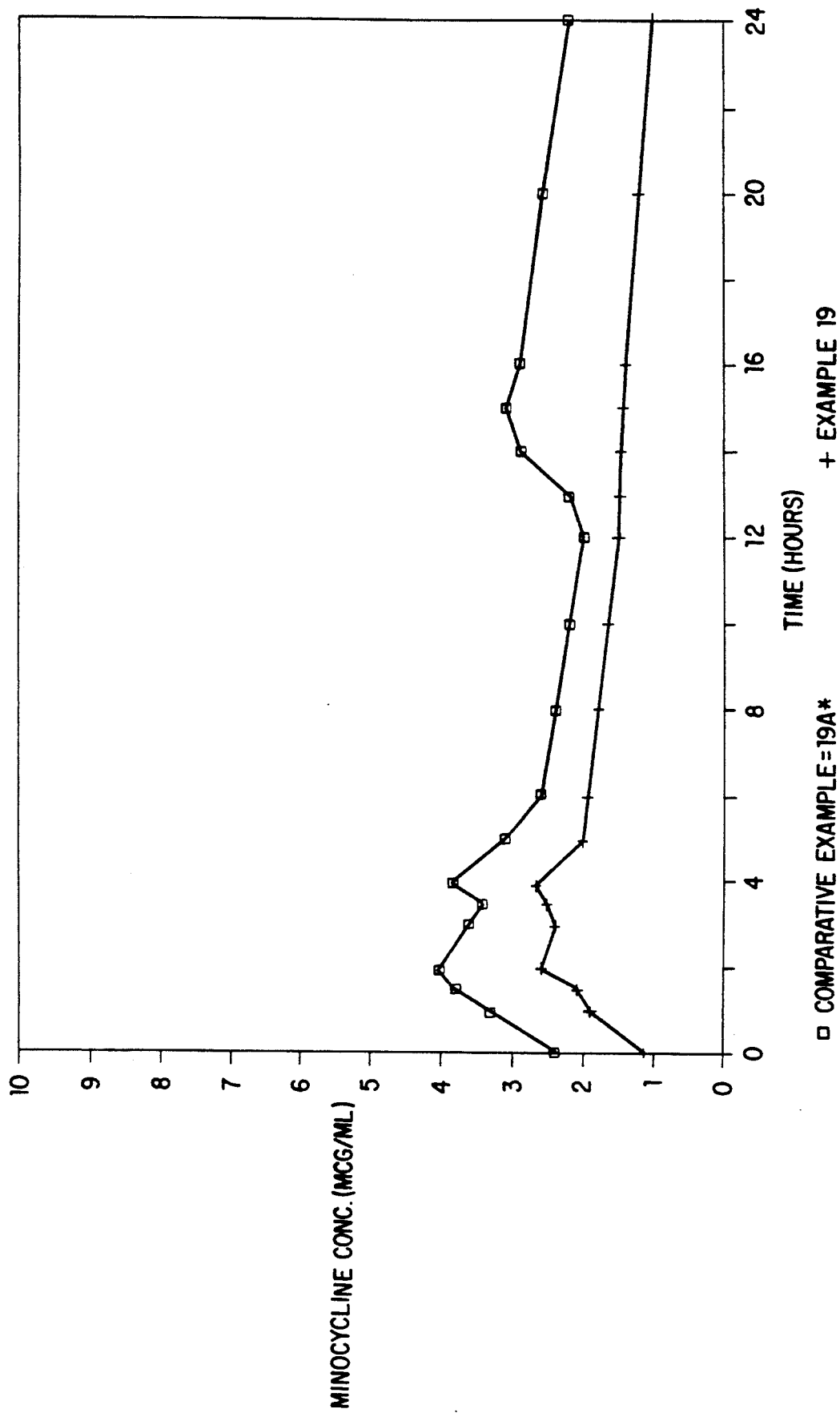
FIG. 12 is a graphic illustration of blood serum concentration levels on the third consecutive day of once-a-day minocycline administration to human subjects in oral dosage unit forms according to the present invention and on the third consecutive day of minocycline administration comprising an initial loading single administration of two oral dosage unit forms presently available from Lederle Laboratories followed by a single oral dosage form presently available from Lederle Laboratories every 12 hours (twice-a-day).

The once-a-day regimen is carried out for three days, and serum concentration levels for the twenty-four hour period commencing with the beginning of day three are measured over that subsequent 24 hour period. The results appear in FIG. 12 in the curve referred to as "Example 19".

COMPARATIVE EXAMPLE 19A*

Two capsules, each containing 100 mg of minocycline hydrochloride powder (Minocin®—Lederle Laboratories), are administered as a loading dose to a human subject. Over the following three days, one capsule containing 100 mg of minocycline hydrochloride powder (Minocin®) is administered every 12 hours.

Serum concentration levels are measured over the initial 12 hour period of administration. The results appear in FIG. 13 in the curve identified as "Comparative Example 19A*".

Serum concentration levels for the 24 hour period commencing with the beginning of day three are measured over the subsequent 24 hour period. The results appear in FIG. 12 in the curve refered to as "Comparative Example 19A*".

EXAMPLE 20

The mixture prepared by the method of Example 17 is pressed into tablets to form oral dosage unit forms having a total minocycline content of 185 mg, with 85 mg of minocycline contained in the quick release granules and 100 mg of the tetracycline compound contained in the pH sensitive polymer coated spherical granules.

EXAMPLE 21

690 grams of the quick release granules prepared by the method of Example 1 and 810 grams of the pH sensitive polymer coated spherical granules prepared by the method of Example 7 are mixed in a low shear blender at low speed for 15 minutes to form a spheronized pharmaceutical composition mixture.

EXAMPLE 22

The mixture prepared by the method of Example 21 is filled into hard shell gelatin capsules to form oral dosage unit forms having a total minocycline content of 185 mg, with 85 mg of the minocycline contained in the quick release granules and 100 mg of the tetracycline compound contained in the pH sensitive polymer coated spherical granules.

Bioavailability is determined to be 76 percent by measuring the area under the plasma concentration curve and comparing that area to that of a reference curve from Comparative Example 22A*.

Figure 14:
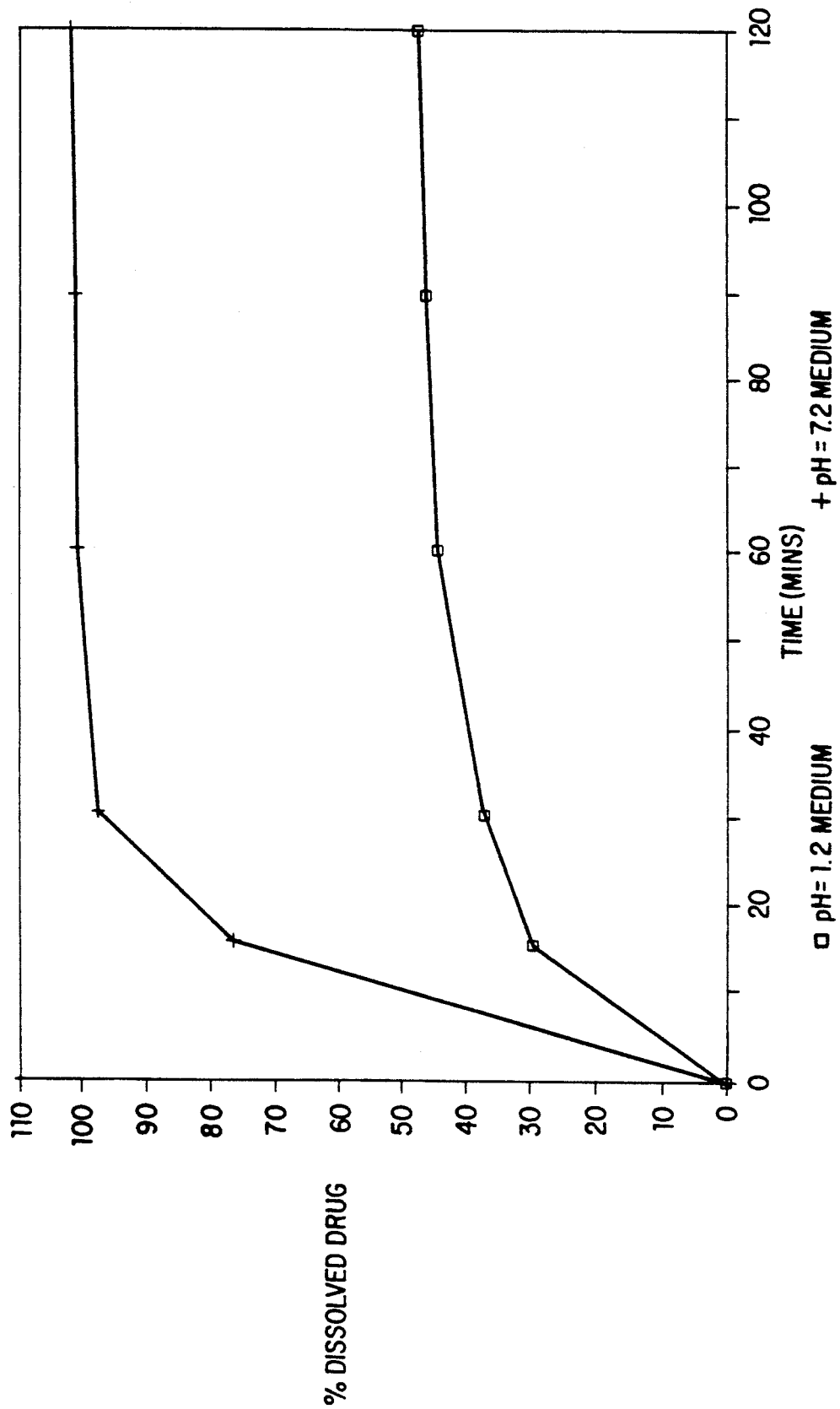
FIG. 14 is a graphic illustration of the release rate of minocycline from capsules containing a mixture of quick release granules adapted to release minocycline in the stomach and pH sensitive polymer coated spherical granules adapted to release minocycline in a medium having a pH of greater than about 5.5 in accordance with the present invention.

Dissolution profiles of the minocycline are determined by U.S.P. XXI test methods using dissolution media with pH's of 1.2 and of 7.2. The results appear in FIG. 14 in graph form.

One capsule is administered to a human subject, and serum concentration levels of minocycline are measured over a 24 hour period. The results appear in FIG. 10 in the curve referred to as "Example 22". A maximum serum concentration of minocycline of 1.9 mcg/ml of serum is reached after 3.8 hours.

Figure 15:
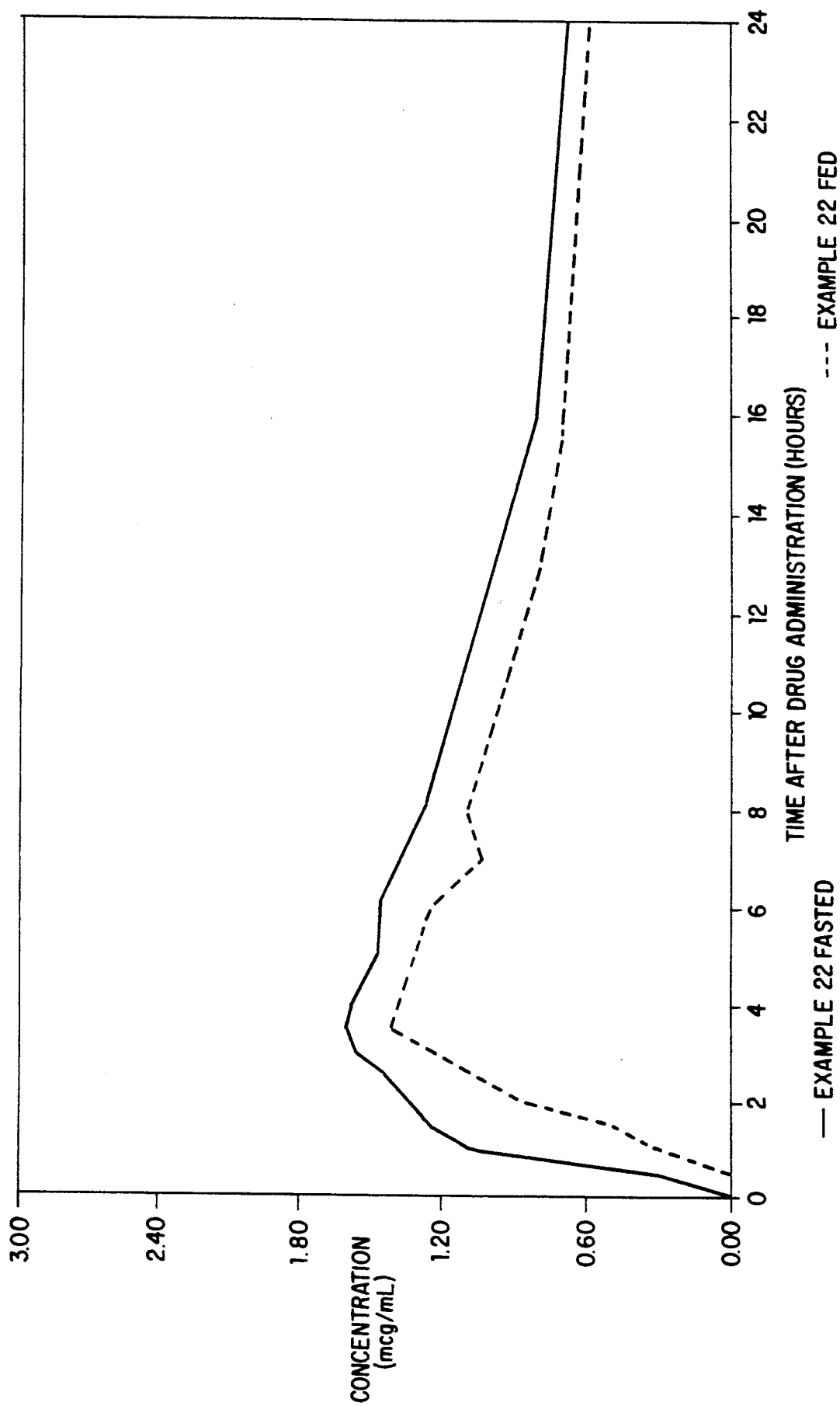
FIG. 15 is a graphic illustration of blood serum concentration levels of minocycline administered to fasting and to non-fasting human subjects in oral dosage unit form capsules containing a mixture of quick release granules adapted to release minocycline in the stomach and pH sensitive polymer coated spherical granules adapted to release minocycline in a medium having a pH of greater than about 5.5 in accordance with the present invention.

One capsule is administered to each of a fasting subject and a subject who eats regularly. Serum concentration levels of tetracycline compound are measured over a 24 hour period. The results illustrating that plasma concentration levels of minocycline of greater than a minimum therapeutically effective serum concentration were maintained for over about 24 hours appear in FIG. 15 in graph form.

COMPARATIVE EXAMPLE 22A*

One capsule containing 100 mg of minocycline hydrochloride powder (Minocin®—Lederle Laboratories) is administered to a human subject, and serum concentration levels of minocycline hydrochloride are measured over a twelve hour period. A second capsule containing 100 mg of minocycline hydrochloride powder (Minocin®) is administered to the subject at the end of the twelve hour period, and serum concentration levels of minocycline hydrochloride are measured over the next twelve hour period. The results appear in FIG. 10 in the curve identified as "Comparative Example 22A*".

Bioavailability is 100 percent as this is the reference for comparison.

A maximum serum concentration of minocycline hydrochloride during the first twelve hour period of 1.78 mcg/ml of serum is reached after 1.5 hours, and a maximum serum concentration of minocycline hydrochloride during the second twelve hour period of 2.65 mcg/ml is reached 1.8 hours after the administration of the second capsule. Minocycline hydrochloride plasma level concentration fluctuates broadly can result in undesirable side effects such as nausea and gastroirritability.

EXAMPLE 23

A multi-coated composition as illustrated in FIG. 4 is prepared.

A core is formed from minocycline (1).

A pH sensitive polymer coating (3) dissolvable in a medium having a pH of about 5.0 is prepared by mixing 75 parts of hydroxypropyl methylcellulose phthalate (HP-50, Shin-Etsu Chemical, Tokyo, Japan) adapted to dissolve in a medium having a pH of about 5.0, 15 parts of mineral oil, and 10 parts of orange colorant (Opaspray K-1-2562, Colorcon, Inc., West Point, PA) and dissolving the mixture in an organic solvent.

The polymer coating solution is sprayed onto the core coated at an initial rate of 7 ml/min which is gradually increased to 9 ml/min in a Uni-Glatt Model 82/E dryer until a 16 percent weight gain based upon the weight of the core is achieved. Input air is adjusted to 54° C. while output air is adjusted between 22 and 25° C.

The single coated core is then coated with a quick release coating (5) containing 85 mg of minocycline.

A polymer coating (7) is then prepared by mixing 71 parts of hydroxypropyl methylcellulose adapted to dissolve in a medium having a pH of less than about 3.9, 4 parts of sodium lauryl sulfate and 25 parts of mineral oil and then by adding 7 to 9 times the total weight of the above solids of water. The coating solution is substantially completely dissolvable in a medium having a pH of less than about 3.9. The solution is sprayed onto the quick release dry coated core to a 2 to 10 weight gain based upon the weight of the quick release dry coated core.

EXAMPLE 24

A multi-coated composition as illustrated in FIG. 5 is prepared. A nonpareil seed (9) is formed from a sucrose crystal. The seed is coated with 100 mg of minocycline (1) to form a core which is then coated with a pH sensitive polymer coating (3) dissolvable in a medium having a pH of about 5.0. The pH sensitive polymer coating is prepared by mixing 75 parts of hydroxypropyl methylcellulose phthalate (HP-50, Shin-Etsu Chemical, Tokyo, Japan) adapted to dissolve in a medium having a pH of about 5.0, 15 parts of mineral oil, and 10 parts of orange colorant (Opaspray K-1-2562, Colorcon, Inc., West Point, Penna.) and dissolving the mixture in an organic solvent.

The polymer coating solution is sprayed onto the core at an initial rate of 7 ml/min which is gradually increased to 9 ml/min in a Uni-Glatt Model 82/E dryer until a 16 percent weight gain based upon the weight of the core is achieved. Input air is adjusted to 54° C. while output air is adjusted between 22 and 25° C.

The single coated core is then coated with a quick release coating (5) containing 85 mg of minocycline.

A polymer coating (7) is then prepared by mixing 71 parts of hydroxypropyl methylcellulose adapted to dissolve in a medium having a pH of less than about 3.9, 4 parts of sodium lauryl sulfate and 25 parts of mineral oil and then by adding 7 to 9 times the total weight of the above solids of water. The coating solution is substantially completely dissolvable in a medium having a pH of less than about 3.9. The solution is sprayed onto the quick release dry coated core to a 2 to 10 parts by weight gain based upon the weight of the quick release dry coated core.

Examples 3 (FIG. 6), 7 (FIG. 7), 8 (FIG. 8), and 11 (FIG. 9) demonstrate the selective release properties of pH sensitive polymer coated release spherical granules.

Example 22 demonstrates the ability of compositions and oral dosage unit forms of the present invention to maintain superior prolonged and controlled release of minocycline and thusly the ability to provide a relatively even, at least minimum therapeutic blood concentration level of minocycline for up to about 24 hours with only once-a-day administration.

Comparative Examples 19A* and 22A* illustrate the uneven release rate and the broad fluctuations in blood levels of minocycline that result from conventional minocycline dosages.

Example 22 further demonstrates that the prolonged controlled release properties are also maintained in a fasting patient, thereby obviating the need for a patient to eat regularly for a therapeutic effect.

Example 19 also demonstrates that the prolonged controlled release properties of dosage unit forms of the present invention are maintained even after three days of continued administration and showing that continued use of the present invention does not impair its prolonged controlled release properties. Comparative Example 19A*, in contrast, demonstrates that traditional dosage forms of minocycline, even after three days of administration still give uneven release with great blood level fluctuations and may consequently result in undesirable side effects.

Comparative Examples 19A* and 22A* further illustrate the inability of conventional oral dosage unit forms to maintain minimum therapeutic concentration levels for prolonged periods of time. The effectiveness of the initial dosaging rapidly subsides after about 12 hours as evidenced by the relatively slight increases over initial concentration achieved after the administration of a second dosage at approximately 12 hours.

Comparative Example 19A* illustrates, when compared with Examples 19 and 22, that the relatively low dosages of the present invention provide relatively even therapeutically effective concentration levels of minocycline.

Examples 20 and 22 demonstrate the pH sensitive properties of the compositions and oral dosage unit forms of the present invention.

All patents, applications, publications and test methods mentioned above are hereby incorporated by reference.

Many variations of the present invention will suggest themselves to those skilled in the art in light of the above detailed description. For example, the separate administration units can be different oral dosage unit forms such as liquid and capsule, tablet and capsule, or tablet and liquid. All such modifications are within the full intended scope of the appended claims.

We claim:

1. A pharmaceutical delivery system adapted to provide a therapeutically effective blood concentration level of 7-dimethylamino-6-deoxy-6-demethyltetracycline or a non-toxic acid addition salt thereof for a sustained period of time of up to about twenty-four hours comprising:
   (I) a multiple delivery vehicle system comprising
      (A) an initial loading therapeutically effective number of quick release granules which comprise
         (a)
            (i) an effective amount of at least one pharmaceutically acceptable excipient; and
            (ii) an effective antibacterial amount of 7-dimethylamino-6-deoxy-6-demethyltetracycline or a non-toxic acid addition salt thereof, on or in said quick release granules; and optionally
         (b) a substantially uniform polymer coating, on said quick release granules and which is rapidly and substantially completely erodible in a medium having a pH of less than about 3.9; said quick release granules being adapted to release substantially completely said minocycline in a medium having a pH of less than about 3.9;
(A-1) an initial loading therapeutically effective amount of finely divided powder comprising
  (a) an effective antibacterial amount of 7-dimethylamino-6-deoxy-6-demethyltetracycline or a non-toxic acid addition salt thereof;
(b) an independent effective amount of at least one pharmaceutically acceptable excipient which may be the same as or different than (I)(A)(a)(i); or
(A-2) an initial loading therapeutically effective combination of (A) and (A-1); and
(B) a secondary loading therapeutically effective number of pH sensitive polymer coated spherical granules which comprise
  (a)
    (i) an independent effective amount of at least one pharmaceutically acceptable excipient which may be the same as or different than (I)(A)(a)(i) or (I)(A-1)(b); and
    (ii) an independent effective antibacterial amount of 7-dimethylamino-6-deoxy-6-demethyltetracycline or a non-toxic acid addition salt thereof, on or in said coated spherical granules; and
  (b) a substantially uniform pH sensitive polymer coating, the polymer of which may be the same as or different than (I)(A)(b), on said coated spherical granules and which is rapidly and substantially completely erodible in a medium having a pH in the range of from about 4.0 to about 7.5; said coated spherical granules thereby being adapted to release substantially completely said minocycline in a medium having pH in the range of from about 4.0 to about 7.5; or
(II) one or more multi-coated spheronized pharmaceutical single delivery vehicle compositions comprising:
(A) a core comprised of
  (a) a full or partial secondary loading therapeutically effective antibacterial amount of 7-dimethylamino-6-deoxy-6-demethyltetracycline or a non-toxic acid addition salt thereof; or
  (b) at least one granule comprised of
    (i) an effective amount of at least one pharmaceutically acceptable excipient; and
    (ii) a full or a partial secondary loading therapeutically effective antibacterial amount of 7-dimethylamino-6-deoxy-6-demethyltetracycline or a non-toxic acid addition salt thereof, on or in said granule; having applied thereon
(B) a substantially uniform pH sensitive polymer coating which is rapidly and substantially completely erodible in a medium having a pH in the range of from about 4.0 to about 7.5; said core thereby being adapted to release substantially completely said minocycline in a medium having a pH in the range of from about 4.0 to about 7.5; having applied thereon
(C) a quick release coating comprising a full or partial initial loading therapeutically effective antibacterial amount of 7-dimethylamino-6-deoxy-6-demethyltetracycline or a non-toxic acid addition salt thereof; and optionally having applied thereon
(D)
  (a) a substantially uniform polymer coating, the polymer of which may be the same as or different than (B), and which is rapidly and substantially completely erodible in a medium having a pH of less than about 3.9;
  (b) a polymer overcoat, the polymer of which may be the same of different than (B) or (D)(a), or
  (c) a combination of (a) and thereon (b) wherein the ratio of quick release granules to pH sensitive polymer granules is 30:70 to 70:30.

2. A pharmaceutical delivery system as defined in claim 1 comprising a mixed blend of (I)(A), (I)(A-1), or (I)(A-2) and (I)(B).

3. A pharmaceutical delivery system as defined in claim 1 comprising separate administration units of initial loading component (I)(A), (I)(A-1), or (I)(A-2) for initial administration and secondary loading component (I)(B) for administration up to about 120 minutes after administration of (I)(A), (I)(A-1) or (I)(A-2).

4. A pharmaceutical delivery system as defined in claim 1 wherein greater than about 70 percent of said minocycline in said initial loading component (I)(A), (I)(A-1), (I)(A-2) or (II)(C) is released from said component in less than about 90 minutes when suspended in a medium of aqueous buffer having a pH of less than about 3.9.

5. A pharmaceutical delivery system as defined in claim 1 wherein greater than about 50 percent of said minocycline in said secondary loading component (I)(B) or single coated core (II)(A) and (B) is released from said component or core in less than about 90 minutes when suspended in a medium of aqueous buffer having a pH in the range of from about 4.0 to about 7.5.

6. A pharmaceutical delivery system as defined in claim 1 wherein from about 5 to about 20 percent of said minocycline in said secondary loading component (I)(B) or single coated core (II)(A) and (B) is released from said secondary loading component or single coated core in about 2 hours when suspended in a medium of simulated gastric fluid having a pH of about 1.2 at about 37° C.

7. A pharmaceutical delivery system as defined in claim 1 wherein from about 20 to about 50 percent of said minocycline in said secondary loading component (I)(B) or single coated core (II)(A) and (B) is released from said secondary loading component or single coated core in about 2 hours when suspended in a medium of simulated gastric fluid having a pH of about 1.2 at about 37° C.

8. A pharmaceutical delivery system as defined in claim 1 wherein said minocycline in said quick release granules (I)(A) comprises from about 10 to about 70 parts by weight and said at least one pharmaceutically acceptable excipient in said quick release comprises from about 90 to about 30 parts by weight based upon 100 parts by weight of said minocycline and said excipient combined and said optional polymer coating on said quick release granules comprises from zero to about 10 parts by weight based upon 100 parts by weight of said minocycline and said excipient combined.

9. A pharmaceutical delivery system as defined in claim 8 wherein said minocycline comprises about 50 parts by weight and said at least one pharmaceutically acceptable excipient comprises about 50 parts by weight based upon 100 parts by weight of said minocycline and said excipient combined.

10. A pharmaceutical delivery system as defined in claim 8 wherein said optional polymer coating comprises from about 1 to about 10 parts by weight based upon 100 parts by weight of said minocycline and said excipient combined.

11. A pharmaceutical delivery system as defined in claim 10 wherein said optional polymer coating comprises about 2 parts by weight based upon 100 parts by weight of said minocycline and said excipient combined.

12. A pharmaceutical delivery system as defined in claim 1 wherein said minocycline in said coated spherical granules (I)(B) or in said core (II)(A) comprises from about 10 to about 80 parts by weight and said at least one pharmaceutically acceptable excipient in said coated spherical granules or said core comprises from about 90 to about 20 parts by weight based upon 100 parts by weight of said minocycline and said excipient combined, and said pH sensitive polymer coating comprises from about 5 to about 35 parts by weight based upon 100 parts by weight of said minocycline and said excipient combined.

13. A pharmaceutical delivery system as defined in claim 12 wherein said pH sensitive polymer coating comprises from about 5 to about 25 parts by weight based upon 100 parts by weight of said minocycline and said excipient combined.

14. A pharmaceutical delivery system as defined in claim 12 wherein said minocycline comprises about 60 parts by weight and said excipient comprises about 40 parts by weight based upon 100 parts of said minocycline and said excipient combined, and said polymer coating comprises from about 5 to about 25 parts by weight based upon 100 parts by weight of said minocycline and said excipient combined.

15. A pharmaceutical delivery system as defined in claim 1 containing from about 25 to about 400 mg of 7-dimethylamino-6-deoxy-6-demethyltetracycline or a non-toxic acid addition salt thereof.

16. A pharmaceutical delivery system as defined in claim 15 containing about 80 to about 280 mg of 7-dimethylamino-6-deoxy-6-demethyltetracycline or a non-toxic acid addition salt thereof.

17. A pharmaceutical delivery system as defined in claim 15 wherein said initial loading (I)(A), (I)(A-1), (I)(A-2) or (II)(C) contains from about 20 to about 200 mg of 7-dimethylamino-6-deoxy-6-dimethyltetracycline or a non-toxic acid addition salt thereof.

18. A pharmaceutical delivery system as defined in claim 15 wherein said pH sensitive polymer coated spherical granules (I)(B) or said core (II)(A) contains from about 20 to about 200 mg of 7-dimethylamino-6-deoxy-6-demethyltetracycline or a non-toxic acid addition salt thereof.

19. A pharmaceutical delivery system as defined in claim 1 wherein said excipient in said quick release granules (I)(A), said powder (I)(A-1), said coated spherical granules (I)(B), said core (II)(A), or a combination thereof, independently, comprises lactose, other mono- or di-saccharides, microcrystalline cellulose, starch, sodium carboxymethyl cellulose, hydroxypropyl cellulose, hydroxyethyl cellulose, crosscarmellose sodium, pregelatinized starch, polyvinylpyrrolidone, crosslinked polyvinylpyrrolidone, hydroxypropylmethyl cellulose, cellulose acetate, hydroxypropyl methylcellulose phthalate, polyvinyl acetate phthalate, microcrystalline cellulose in combination with lactose, microcrystalline cellulose in combination with sodium carboxymethyl cellulose, microcrystalline cellulose in combination with crosscarmellose sodium, or a mixture of any of the foregoing.

20. A pharmaceutical delivery system as defined in claim 19 wherein said excipient in said quick release granules (I)(A) or said core (II)(A) comprises microcrystalline cellulose.

21. A pharmaceutical delivery system as defined in claim 19 wherein said excipient in said coated spherical granules (I)(B) comprises microcrystalline cellulose in combination with crosscarmellose sodium.

22. A pharmaceutical delivery system as defined in claim 1 wherein said pH sensitive polymer coating is selected from
 (a) methylcellulose
 (b) ethylcellulose
 (c) hydroxyethyl cellulose
 (d) hydroxypropyl cellulose
 (e) hydroxypropyl methylcellulose
 (f) hydroxypropyl methylcellulose phthalate
 (g) cellulose acetate phthalate
 (h) hydroxypropyl methylcellulose succinate
 (i) a polymer or copolymer of (meth)acrylic acid or an ester thereof
 (j) polyvinyl acetate phthalate
 (k) a polymer or copolymer of polyvinyl acetate
 (l) cellulose acetate
 (m) fatty acids and esters thereof
 (n) cellulose acetate trimellitate; or
 (o) a mixture of any of the foregoing, alone, or in further combination with a plasticizer, a colorant, or a pigment; adapted to dissolve substantially completely in a medium having a pH in the range of from about 4.0 to about 7.5.

23. A pharmaceutical delivery system as defined in claim 22 wherein said polymer coating comprises hydroxypropyl methylcellulose phthalate adapted to dissolve substantially completely in a medium having a pH of about 5.0.

24. A pharmaceutical delivery system as defined in claim 22 wherein said polymer coating comprises a combination of hydroxypropyl methylcellulose phthalate and hydroxypropyl methylcellulose adapted to dissolve substantially completely in a medium having a pH of about 4.0 to about 7.5.

25. A pharmaceutical delivery system as defined in claim 22 wherein said polymer coating comprises hydroxypropyl methylcellulose phthalate adapted to dissolve substantially completely in a medium having a pH of greater than about 5.5.

26. A method of maintaining a therapeutically effective level of 7-dimethylamino-6-deoxy-6-demethyltetracycline or a non-toxic acid addition salt thereof in the blood stream of a warm-blooded mammal for about 24 hours comprising the ingestion of a pharmaceutical delivery system as defined in claim 1.

27. A pharmaceutical delivery system as defined in claim 1 wherein said optional polymer coating on said quick release granules or said optional uniform polymer coating on said multi-coated composition is selected from
 (a) methylcellulose
 (b) ethylcellulose
 (c) hydroxyethyl cellulose
 (d) hydroxypropyl cellulose
 (e) hydroxypropyl methylcellulose
 (f) hydroxypropyl methylcellulose phthalate
 (g) cellulose acetate phthalate (h) hydroxypropyl methylcellulose succinate
(i) a polymer or copolymer of (meth)acrylic acid or an ester thereof
(j) polyvinyl acetate phthalate
(k) a polymer or copolymer of polyvinyl acetate
(l) cellulose acetate
(m) fatty acids and esters thereof
(n) cellulose acetate trimellitate; or
(o) a mixture of any of the foregoing, alone, or in further combination with a plasticizer, a colorant, or a pigment; adapted to dissolve substantially completely in a medium having a pH of less than about 3.9.

28. A pharmaceutical delivery system as defined in claim 27 wherein said optional polymer coating comprises hydroxypropyl methylcellulose.

29. A pharmaceutical delivery system as defined in claim 1 wherein said pH sensitive polymer coated spherical granules, said quick release granules, or both, independently, have an average diameter in the range of from about 0.1 to about 2.5 millimeters.

30. A pharmaceutical delivery system as defined in claim 29 wherein said pH sensitive polymer coated spherical granules, said quick release granules, or both, independently, have an average diameter in the range of from about 0.8 to about 1.2 millimeters.

31. A pharmaceutical delivery system as defined in claim 1 wherein said polymer coating on said quick release granules, said coated spherical granules or a combination of the foregoing, independently also, includes a precoating under, an overcoating over or a combination thereof in addition to the pH sensitive polymer coating, of the same or a different polymer.

32. A pharmaceutical delivery system as defined in claim 31 wherein said precoating, overcoating or combination thereof comprises from about 1 to about 10 parts by weight of said pH sensitive polymer coated release spherical granules.

33. A controlled release pharmaceutical composition in oral dosage unit form comprising a hard or a soft shell capsule at least partially filled with a pharmaceutical delivery system as defined in claim 1.

34. An oral dosage unit as defined in claim 33 which also includes a lubricant, a disintegrant, a plasticizer, a colorant, a pigment, a flavoring, an additional medicament, or a combination of any of the foregoing.

* * * * *